United States Patent
Griffin et al.

(10) Patent No.: US 11,191,486 B2
(45) Date of Patent: Dec. 7, 2021

(54) SYSTEM AND METHOD FOR DETECTING DECOUPLING OF AN AUSCULTATORY SOUND SENSOR FROM A TEST-SUBJECT

(71) Applicant: AUSCULSCIENCES, INC., Vienna, VA (US)

(72) Inventors: Robert J. Griffin, Richmond Hill (CA); Daniel Labonté, Ottawa (CA); Md Shahidul Islam, Ottawa (CA); Simon Martin, Gatineau (CA); Camilla Jastrzebski, Ottawa (CA); Brady Laska, Arnprior (CA); David Gloag, Kanata (CA); Sergey A. Telenkov, Ottawa (CA)

(73) Assignee: AusculSciences, Inc., Vienna, VA (US)

( * ) Notice: Subject to any disclaimer, the term of this patent is extended or adjusted under 35 U.S.C. 154(b) by 86 days.

(21) Appl. No.: 16/136,015

(22) Filed: Sep. 19, 2018

(65) Prior Publication Data
US 2019/0083038 A1    Mar. 21, 2019

Related U.S. Application Data

(60) Provisional application No. 62/560,568, filed on Sep. 19, 2017, provisional application No. 62/568,155, (Continued)

(51) Int. Cl.
*A61B 7/04* (2006.01)
*A61B 5/00* (2006.01)
(Continued)

(52) U.S. Cl.
CPC .......... *A61B 5/6844* (2013.01); *A61B 5/7246* (2013.01); *A61B 7/04* (2013.01);
(Continued)

(58) Field of Classification Search
CPC .......... A61B 7/00; A61B 7/003; A61B 7/006; A61B 7/008; A61B 7/02; A61B 7/026;
(Continued)

(56) References Cited

U.S. PATENT DOCUMENTS 4,308,870 A    1/1982    Arkans
4,509,527 A    4/1985    Fraden
(Continued)

FOREIGN PATENT DOCUMENTS

DE    3531399 A1    3/1986
GB    2166871 A    5/1986
(Continued)

OTHER PUBLICATIONS

Perini et al., "Body Position Affects the Power Spectrum of Heart Rate Variability During Dynamic Exercise," 66 Eur. J. Appl. Physiol., pp. 207-213 (1993).
(Continued)

*Primary Examiner* — Ahmed M Farah
(74) *Attorney, Agent, or Firm* — Kurt L. VanVoorhies

(57) ABSTRACT

At least one of at least one data-dependent scale factor or at least one data-dependent detection threshold is determined responsive to at least one block of time-series data of an auscultatory-sound signal generated by an auscultatory-sound sensor operatively coupled to a portion of the skin of a test-subject, wherein the at least one data-dependent scale factor or at least one data-dependent detection threshold provides a measure of a range of values of the at least one block of time-series data in relation to a predetermined metric, and is used to determine whether or not the auscultatory-sound sensor is either debonded or detached from the skin of the test-subject.

27 Claims, 22 Drawing Sheets

Related U.S. Application Data filed on Oct. 4, 2017, provisional application No. 62/575,364, filed on Oct. 20, 2017, provisional application No. 62/575,383, filed on Oct. 21, 2017.

(51) Int. Cl.

| | |
|---|---|
| *G06F 16/68* | (2019.01) |
| *H04B 1/38* | (2015.01) |
| *A61B 7/02* | (2006.01) |
| *A61B 5/02* | (2006.01) |
| *A61B 5/318* | (2021.01) |

(52) U.S. Cl.
CPC ........ *G06F 16/686* (2019.01); *A61B 5/02007* (2013.01); *A61B 5/318* (2021.01); *A61B 5/6843* (2013.01); *A61B 5/7221* (2013.01); *A61B 7/026* (2013.01); *A61B 2560/0456* (2013.01); *A61B 2560/0475* (2013.01); *A61B 2562/0204* (2013.01); *A61B 2562/0219* (2013.01); *H04B 1/38* (2013.01)

(58) Field of Classification Search
CPC .. A61B 7/04; A61B 7/045; A61B 5/72; A61B 5/7203; A61B 5/7221; A61B 5/7246; A61B 5/725; A61B 5/7253; A61B 5/7257; A61B 5/02; A61B 5/02028; A61B 5/0205; A61B 5/021; A61B 5/02108; A61B 2562/0204; A61B 2562/0219; A61B 2562/0247; A61B 2562/0261; A61B 5/68; A61B 5/6801; A61B 5/683; A61B 5/6843; A61B 5/6844; G10L 25/03; G10L 25/06; G10L 25/21; G10L 25/27; G10L 25/48; G10L 25/51; G10L 25/66; G10L 25/69; G10L 25/78; G10L 2025/786; G10L 25/84; G10L 21/0208; G10L 2021/02082; G10L 2021/020825; G10L 21/0216; G10L 2021/02161; G10L 21/0224; G10L 21/0232; G10L 21/0264; G10L 21/0272; G10L 21/028; G10L 21/0308; G10L 21/0324; G10L 21/0332; G10L 21/0356; G10L 21/0364
USPC ................ 600/481–484, 508, 514, 528, 586; 128/898
See application file for complete search history.

(56) References Cited

U.S. PATENT DOCUMENTS

| | | | |
|---|---|---|---|
| RE32,180 E | 6/1986 | Lewiner | |
| 4,628,939 A | 12/1986 | Little | |
| 4,862,144 A | 8/1989 | Tao | |
| 4,967,760 A | 11/1990 | Bennett, Jr. et al. | |
| 5,002,060 A | 3/1991 | Nedivi | |
| 5,105,354 A | 4/1992 | Nishimura | |
| 5,309,922 A | 5/1994 | Schechter | |
| 5,632,272 A | 5/1997 | Diab | |
| 5,687,738 A | 11/1997 | Shapiro et al. | |
| 5,909,495 A | 6/1999 | Andrea | |
| 5,957,855 A | 9/1999 | Oriol | |
| 5,957,866 A | 9/1999 | Shapiro et al. | |
| 6,002,777 A | 12/1999 | Grasfield | |
| 6,005,951 A | 12/1999 | Grasfield | |
| 6,050,950 A | 4/2000 | Mohler | |
| 6,053,872 A | 4/2000 | Mohler | |
| 6,152,879 A | 11/2000 | Mohler | |
| 6,179,783 B1 | 1/2001 | Mohler | |
| 6,278,890 B1 | 8/2001 | Chassaing et al. | |
| 6,478,744 B2 | 11/2002 | Mohler | |
| 6,491,647 B1 | 12/2002 | Bridger et al. | |
| 6,572,560 B1 | 6/2003 | Watrous et al. | |
| 6,699,204 B1 | 3/2004 | Kehyayan et al. | |
| 6,898,459 B2 | 5/2005 | Hayek et al. | |
| 6,953,436 B2 | 10/2005 | Watrous et al. | |
| 7,389,136 B2 | 6/2008 | Avinash et al. | |
| 7,416,531 B2 | 8/2008 | Mohler | |
| 8,133,176 B2 | 3/2012 | Porges et al. | |
| 8,419,651 B2 | 4/2013 | Owsley et al. | |
| 8,657,742 B2 | 2/2014 | Neumann | |
| 8,696,585 B2 | 4/2014 | Addison et al. | |
| 8,870,792 B2 | 10/2014 | Al-Ali et al. | |
| 8,961,427 B2 | 2/2015 | Owsley et al. | |
| 8,972,197 B2 | 3/2015 | Jangle et al. | |
| 9,192,351 B1 | 11/2015 | Telfort et al. | |
| 9,510,775 B2 | 12/2016 | Morren et al. | |
| 9,591,972 B1 | 3/2017 | Owsley et al. | |
| 9,675,282 B2 | 6/2017 | Morren | |
| 9,955,939 B2 | 5/2018 | Sezan et al. | |
| 10,194,885 B2* | 2/2019 | Byrd | A61B 5/7405 |
| 10,555,717 B2 | 2/2020 | Hsu et al. | |
| 11,045,144 B2* | 6/2021 | Zhou | A61B 5/318 |
| 2008/0221418 A1 | 9/2008 | Al-Ali et al. | |
| 2010/0189276 A1 | 7/2010 | Andersen | |
| 2011/0046499 A1 | 2/2011 | Klewer et al. | |
| 2011/0066041 A1 | 3/2011 | Pandia et al. | |
| 2011/0066042 A1 | 3/2011 | Pandia et al. | |
| 2011/0098583 A1 | 4/2011 | Pandia et al. | |
| 2011/0125060 A1 | 5/2011 | Telfort et al. | |
| 2012/0029375 A1 | 2/2012 | Lane et al. | |
| 2012/0130263 A1* | 5/2012 | Pretorius | A61B 5/349 |
| | | | 600/509 |
| 2013/0261484 A1* | 10/2013 | Schmidt | A61B 5/725 |
| | | | 600/528 |
| 2015/0011913 A1 | 1/2015 | Fuke et al. | |
| 2015/0164380 A1 | 6/2015 | O'Dwyer et al. | |
| 2016/0007923 A1 | 1/2016 | Yamamoto | |
| 2017/0079594 A1 | 3/2017 | Telfort et al. | |
| 2018/0317876 A1* | 11/2018 | Emmanouilidou | G06N 99/00 |
| 2019/0117162 A1* | 4/2019 | Zhou | A61B 5/0402 |
| 2019/0298183 A1 | 10/2019 | Burg et al. | |
| 2020/0245889 A1* | 8/2020 | Telenkov | A61B 5/316 |

FOREIGN PATENT DOCUMENTS

| | | |
|---|---|---|
| JP | 3035983 U | 4/1997 |
| JP | 3141674 B2 | 3/2001 |
| JP | 2008302052 A | 12/2008 |
| JP | 2009261518 A | 11/2009 |
| JP | 2011044909 A | 3/2011 |
| JP | 2012200382 A1 | 10/2012 |
| JP | 5141361 B2 | 2/2013 |
| JP | 2014052553 A | 3/2014 |
| JP | 6065308 B2 | 1/2017 |
| WO | 9923940 A1 | 5/1999 |
| WO | 2006067217 A2 | 6/2006 |
| WO | 2010038123 A1 | 4/2010 |
| WO | 2017042875 A1 | 3/2017 |

OTHER PUBLICATIONS

European Patent Office International Search Report and Written Opinion of International Searching Authority in International Application No. PCT/US2018/051813, dated Jan. 28, 2019, 9 pp.
European Patent Office Communication Pursuant to Article 94(3) EPC in European Application No. 18793292.6, dated Jun. 17, 2021, 4 pp.

* cited by examiner

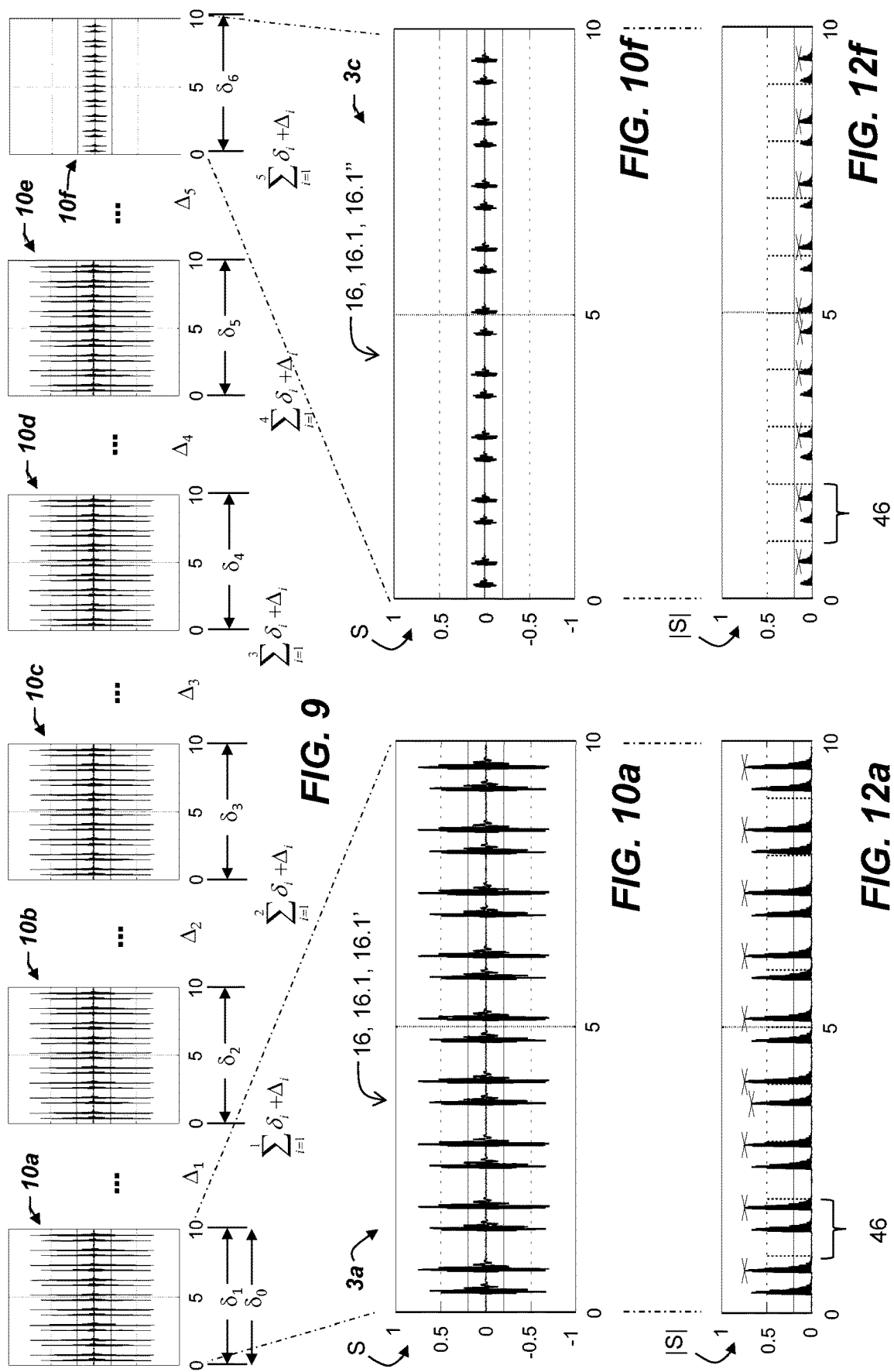

SYSTEM AND METHOD FOR DETECTING DECOUPLING OF AN AUSCULTATORY SOUND SENSOR FROM A TEST-SUBJECT

CROSS-REFERENCE TO RELATED APPLICATIONS

The instant application claims the benefit of the following: U.S. Provisional Application Ser. No. 62/560,568 filed on 19 Sep. 2017, U.S. Provisional Application No. 62/568,155 filed on 4 Oct. 2017, U.S. Provisional Application No. 62/575,364 filed on 20 Oct. 2017, and U.S. Provisional Application Ser. No. 62/575,383 filed on 21 Oct. 2017, each of which is incorporated herein by reference in its entirety.

BRIEF DESCRIPTION OF THE DRAWINGS

In the accompanying drawings:

FIGS. 5b and 5c each illustrate an auscultatory sound sensor that is detached, and therefore fully decoupled, from the skin of a test-subject, wherein FIG. 5b illustrates the associated adhesive interface detached from the skin of the test-subject, and FIG. 5c illustrates the associated adhesive interface detached from the auscultatory sound sensor;

FIG. 9 illustrates a plurality of six blocks of breath-held, auscultatory-sound-sensor time-series data recorded from an auscultatory sound sensor coupled to the skin of the thorax of a test-subject being diagnosed for a prospective abnormal cardiovascular condition;

FIGS. 10a-10f respectively illustrate a simulation of successively recorded blocks of breath-held, sensor time-series data illustrated in FIG. 9, each illustrated with an expanded time scale, wherein FIGS. 10a-10e illustrates a condition for which the auscultatory sound sensor is coupled to the skin of the test-subject, and FIG. 10f illustrates a condition for which the auscultatory sound sensor is decoupled from the skin of the test-subject;

FIGS. 12a-12f respectively illustrate time-series of the absolute values of the corresponding time-series data illustrated in FIGS. 10a-10f, further illustrating a division of the block of breath-held, sensor time-series data into a plurality of associated data segments, with each data segment of sufficient width to nominally include sound from a single heartbeat, and with the peak values in each data segment marked, wherein FIGS. 12a-12e illustrates a condition for which the auscultatory sound sensor is coupled to the skin of the test-subject, and FIG. 12f illustrates a condition for which the auscultatory sound sensor is decoupled from the skin of the test-subject;

DESCRIPTION OF EMBODIMENT(S)

Figure 1:
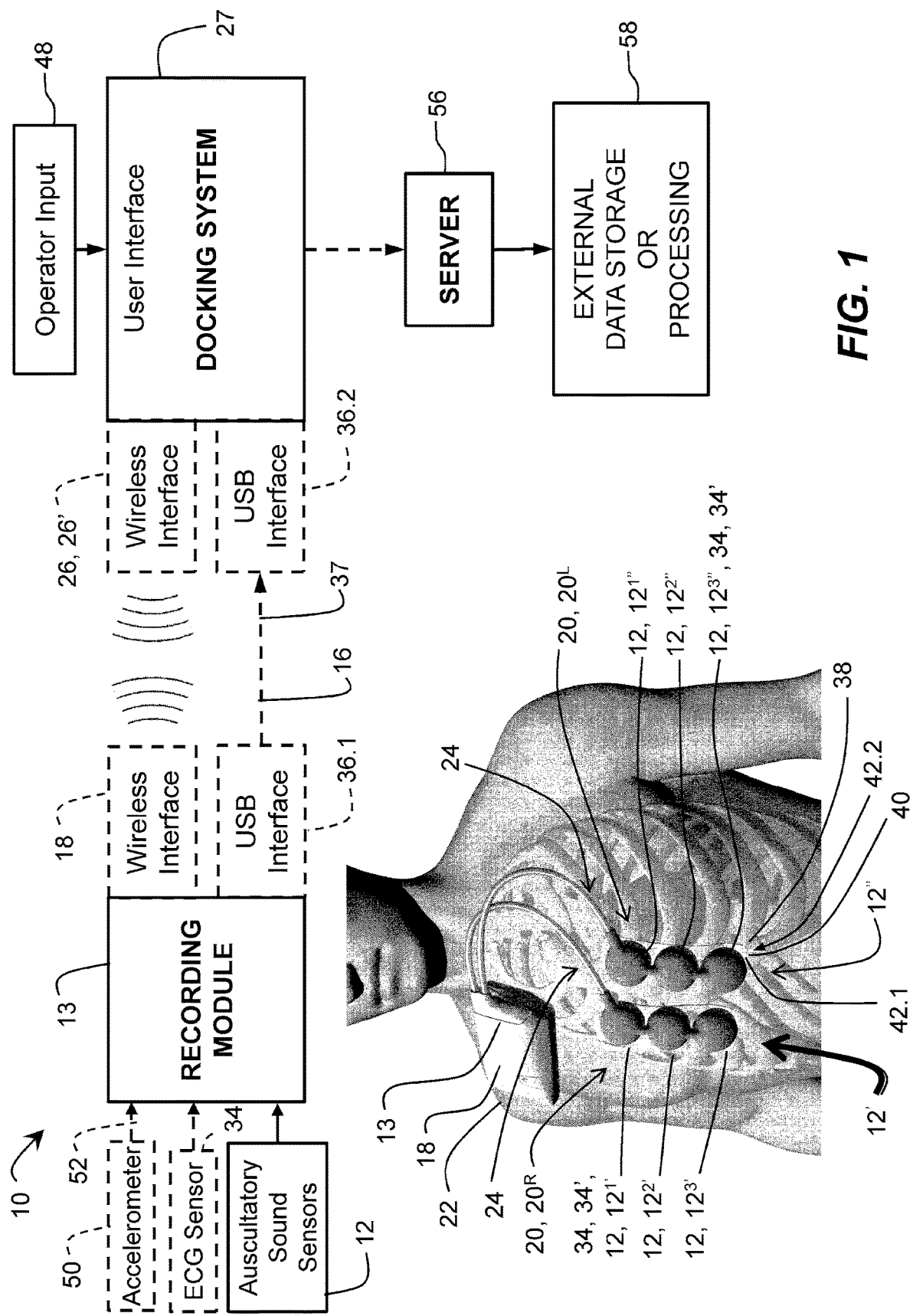
FIG. 1 illustrates a block diagram of a coronary-artery-disease detection system.
Figure 2:
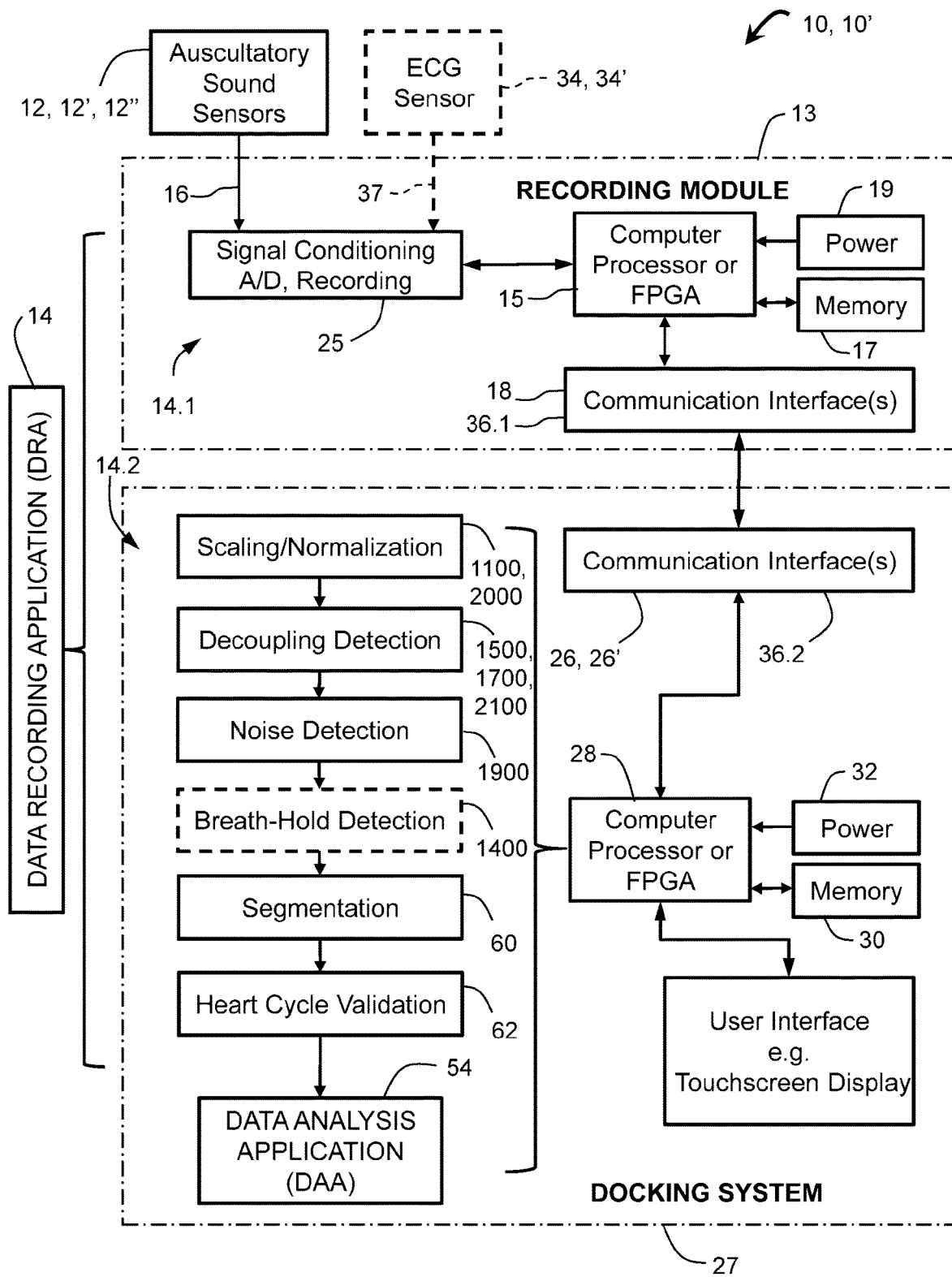
FIG. 2 illustrates a first aspect of a data recording module and a first aspect of an associated docking system, in accordance with a first aspect of the coronary-artery-disease detection system illustrated in FIG. 1.
Figure 3:
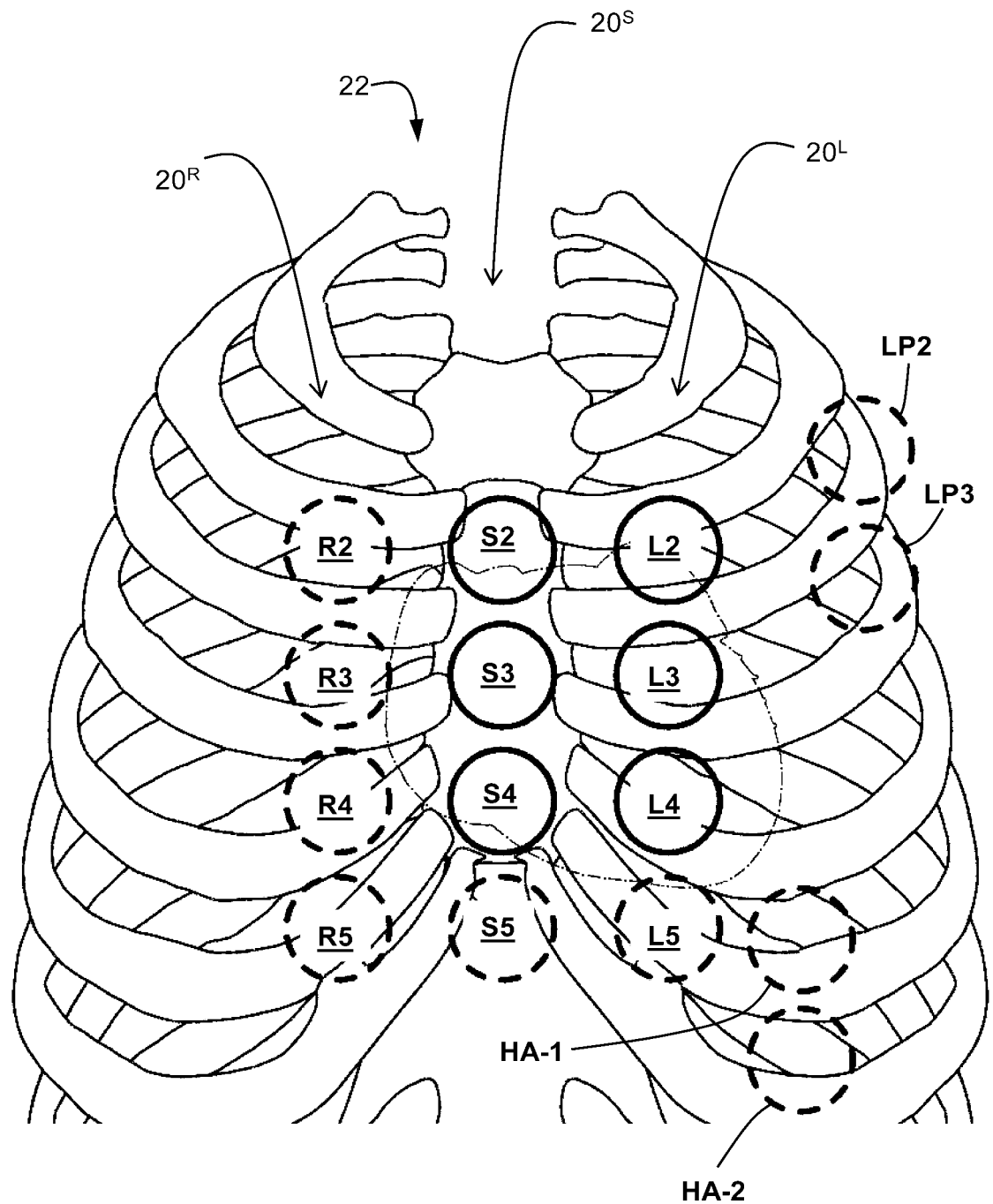
FIG. 3 illustrates a fragmentary view of a human thorax and associated prospective locations of auscultatory sound sensors associated right, sternum and left, second, third, fourth and fifth, inter-costal spaces, left posterior locations at the second and third inter-costal spaces, and locations proximate to the heart apex.

Referring to FIGS. 1 and 2, an auscultatory coronary-artery-disease detection system 10 incorporates at least one auscultatory sound sensor 12 that is operatively coupled to a recording module 13 running at least a first portion 14.1 of a Data Recording Application (DRA) 14, 14.1 on a first specialized computer or electronic system comprising a first computer processor or FPGA (Field Programmable Gate Array) 15 and first memory 17 powered by a first power supply 19, which provides for recording and preprocessing auscultatory sound signals 16 from the at least one auscultatory sound sensor 12. For example, in one set of embodiments, the at least one auscultatory sound sensor 12 comprises a first group 12' of three auscultatory sound sensors 12, $12^{1\prime}$, $12^{2\prime}$, $12^{3\prime}$ physically interconnected end-to-end with one another, and physically and electrically interconnected with a first wireless transceiver 18; and a second group 12" of three auscultatory sound sensors 12, $12^{1\prime\prime}$, $12^{2\prime\prime}$, $12^{3\prime\prime}$ physically interconnected end-to-end with one another, and physically and electrically interconnected with the first wireless transceiver 18, with both groups 12', 12" of auscultatory sound sensors placed on the skin of the thorax 20 of a test-subject 22, in acoustic communication therewith. Referring also to FIG. 3, the placement of the first group of auscultatory sound sensors 12' in FIG. 1 is illustrated with the respective associated auscultatory sound sensors 12, $12^{1\prime}$, $12^{2\prime}$, $12^{3\prime}$ in substantial alignment with the corresponding respective third R3, fourth R4 and fifth R5, inter-costal spaces on the right side $20^R$ of the thorax 20, and the placement of the second group of auscultatory sound sensors 12" in FIG. 1 is illustrated with the respective associated auscultatory sound sensors 12, $12^{1\prime\prime}$, $12^{2\prime\prime}$, $12^{3\prime\prime}$ in substantial alignment with the corresponding respective third L3, fourth L4 and fifth L5, inter-costal spaces on the left side $20^L$ of the thorax 20. Prospective sensor locations R2-R5, S2-S5, and L2-L5 illustrated in FIG. 3 respectively refer to the second R2 through fifth R5 inter-costal spaces on the right side $20^R$ of the thorax 20, the second S2 through fifth S5 inter-costal spaces at the center/sternum $20^S$ of the thorax 20, and the second L2 through fifth L5 inter-costal spaces on the left side $20^L$ of the thorax 20. Furthermore, prospective left-side posterior sensor locations LP2 and LP3 illustrated in FIG. 3 respectively refer to at the second LP2 and third LP3 intercostal spaces locations on the posterior of the thorax 20. Yet further, prospective sensor locations HA-1 and HA-2 are proximate to the apex of the heart, either on the anterior or the posterior of the thorax 20. For example, in one set of embodiments. The auscultatory sound sensors 12, $12^{1\prime}$, $12^{2\prime}$, $12^{3\prime}$, $12^{1\prime\prime}$, $12^{2\prime\prime}$, $12^{3\prime\prime}$ are located at the second S2, L2, third S3, L3 and fourth S4, L4 inter-costal spaces at the sternum S2-S4 and left-side L2-L4 of the thorax 20.

As used herein, the term "auscultatory sound" is intended to mean a sound originating from inside a human or animal organism as a result of the biological functioning thereof, for example, as might be generated by action of the heart, lungs, other organs, or the associated vascular system; and is not intended to be limited to a particular range of frequencies— for example, not limited to a range of frequencies or sound intensities that would be audible to a human ear,—but could include frequencies above, below, and in the audible range, and sound intensities that are too faint to be audible to a human ear. Furthermore, the term "auscultatory-sound sensor" is intended to mean a sound sensor that provides for transducing auscultatory sounds into a corresponding electrical or optical signal that can be subsequently processed.

The auscultatory sound sensors 12, $12^{1\prime}$, $12^{2\prime}$, $12^{3\prime}$, $12^{1\prime\prime}$, $12^{2\prime\prime}$, $12^{3\prime\prime}$ provide for transducing the associated sounds received thereby into corresponding auscultatory sound signals 16 that are preprocessed and recorded by an associated hardware-based signal conditioning/preprocessing and recording subsystem 25, then communicated to the first wireless transceiver 18, and then wirelessly transmitted thereby to an associated second wireless transceiver 26 of an associated wireless interface 26' of an associated docking system 27, possibly running a second portion 14.2 of the Data Recording Application (DRA) 14, 14.2 on a corresponding second specialized computer or electronic system comprising an associated second computer processor or FPGA (Field Programmable Gate Array) 28 and second memory 30, both of which are powered by an associated second power supply 32, which together provide for recording and preprocessing the associated auscultatory sound signals 16 from the auscultatory sound sensors 12, $12^{1\prime}$, $12^{2\prime}$, $12^{3\prime}$, $12^{1\prime\prime}$, $12^{2\prime\prime}$, $12^{3\prime\prime}$.

For example, in accordance with one set of embodiments, the hardware-based signal conditioning/preprocessing and recording subsystem 25 includes an amplifier—either of fixed or programmable gain,—a filter and an analog-to-digital converter (ADC). For example, in one set of embodiments, the analog-to-digital converter (ADC) is a 16-bit analog-to-digital converter (ADC) that converts a −2.25 to +2.25 volt input to a corresponding digital value of −32, 768 to +32, 767. Furthermore, in accordance with one set of embodiments of the amplifier, the amplifier gain is programmable to one of sixteen different levels respectively identified as levels 0 to 15, with corresponding, respective gain values of 88, 249, 411, 571, 733, 894, 1055, 1216, 1382, 1543, 1705, 1865, 2027, 2188, 2350 and 2510, respectively for one set of embodiments. In accordance with another set of embodiments of the amplifier, the amplifier gain is fixed at the lowest above value, i.e., for this example, 88, so as to provide for avoiding the relative degradation of the associated signal-to-noise ratio (SNR) that naturally occurs with the relatively high gain levels of the programmable-gain set of embodiments.

It should be understood that the associated processes of the Data Recording Application (DRA) 14 could be implemented either in software-controlled hardware, hardware, or a combination of the two.

For example, in one set of embodiments, either or both the recording module 13 or docking system 27 may be constructed and operated in accordance with the disclosure of U.S. Provisional Application No. 62/575,364 filed on 20 Oct. 2017, entitled CORONARY ARTERY DISEASE DETECTION SYSTEM, which is incorporated by reference in its entirety. Furthermore, in accordance with one set of embodiments, the auscultatory coronary-artery-disease detection system 10 may further incorporate an ECG sensor 34, for example, in one set of embodiments, an ECG sensor 34' comprising a pair of electrodes incorporated in a corresponding pair of auscultatory sound sensors 12, wherein the signal from the ECG sensor 34' is also preprocessed and recorded by a different signal channel of the same hardware-based signal conditioning/preprocessing and recording subsystem 25 of the recording module 13 that is used to preprocess the signals from the one or more auscultatory sound sensors 12. Furthermore, in one set of embodiments, the recording module 13 and docking system 27 may each incorporate a corresponding respective USB interface 36.1, 36.2 to provide for transferring corresponding auscultatory sound signals 16 and or an ECG signal 37 from the recording module 13 to the docking system 27, for example, rather than relying upon the first 18 and second 26 wireless transceivers of an associated wireless interface 26'. Further alternatively, either instead of, or in addition to, the wireless interface 26' or the USB interface 36.1, 36.2, data may be transferred from the recording module 13 to the docking system 27 via a portable memory element, for example, either an SD memory card or a Micro SD memory card.

The functionality of the Data Recording Application (DRA) 14 is distributed across the recording module 13 and the docking system 27. For example, referring to FIG. 2, in accordance with a first aspect 10' of an auscultatory coronary-artery-disease detection system 10, 10', the Data Recording Application (DRA) 14 spans across the recording module 13 and the docking system 27, with a first portion 14.1 comprising the hardware-based signal conditioning/preprocessing and recording subsystem 25 operative on the recording module 13, and a remaining second portion 14.2 operative on the docking system 27. Alternatively, as another example, referring to FIG. 4, in accordance with a second aspect 10" of an auscultatory coronary-artery-disease detection system 10, 10", the Data Recording Application (DRA) 14 is operative on the recording module 13.

The auscultatory sound sensor 12 provides for sensing sound signals that emanate from within the thorax 20 of the test-subject 22 responsive to the operation of the test-subject's heart, and the resulting flow of blood through the arteries and veins, wherein an associated build-up of deposits therewithin can cause turbulence in the associated blood flow that can generate associated cardiovascular-condition-specific sounds, the latter of which can be detected by a sufficiently-sensitive auscultatory sound sensor 12 that is acoustically coupled to the skin 38 of the thorax 20 of the test-subject 22. For some cardiovascular-conditions associated with, or predictive of, a cardiovascular disease, the sound level of these cardiovascular-condition-specific sounds can be below a level that would be detectable by a human using a conventional stethoscope. However, these sound levels are susceptible to detection by sufficiently sensitive auscultatory sound sensor 12 that is sufficiently acoustically coupled to the skin 38 of the thorax 20 of the test-subject 22. For example, in one set of embodiments, the auscultatory sound sensor 12 may be constructed in accordance with the teachings of U.S. Provisional Application No. 62/568,155 filed on 4 Oct. 2017, entitled AUSCULTA-TORY SOUND SENSOR. Furthermore, in another set of embodiments, the auscultatory sound sensor 12 may be constructed in accordance with the teachings of U.S. Pat. Nos. 6,050,950, 6,053,872 or 6,179,783, which are incorporated herein by reference.

Figure 5A:
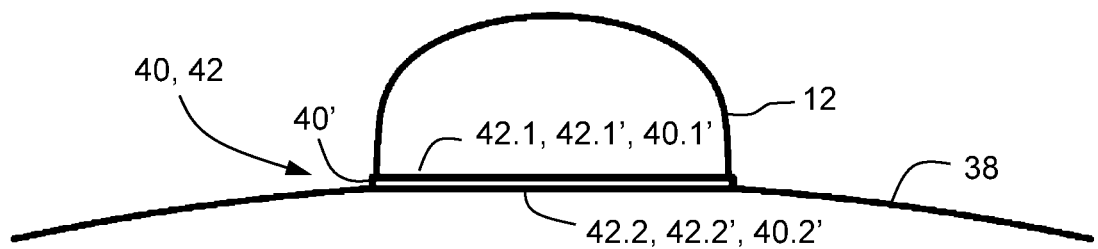
FIG. 5a illustrates an auscultatory sound sensor coupled to the skin of a test-subject, by bonding via associated adhesive layers or surfaces on both sides of an adhesive interface.
Figure 5B:
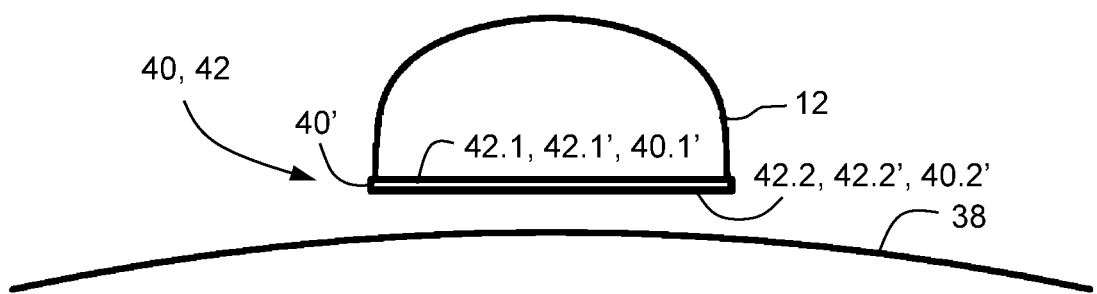
Figure 5C:
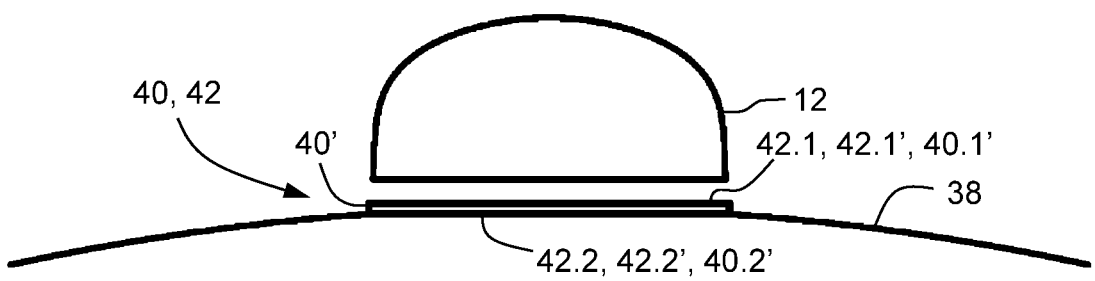
Figure 5D:
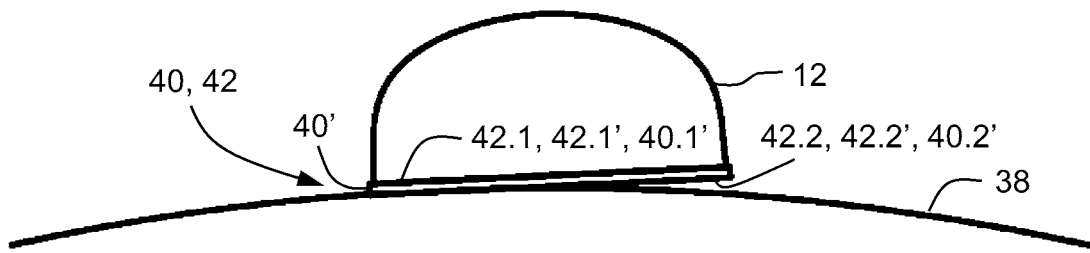
FIGS. 5d through 5g each illustrate an auscultatory sound sensor that is partially coupled to, but debonded from, the skin of a test-subject.
Figure 5E:
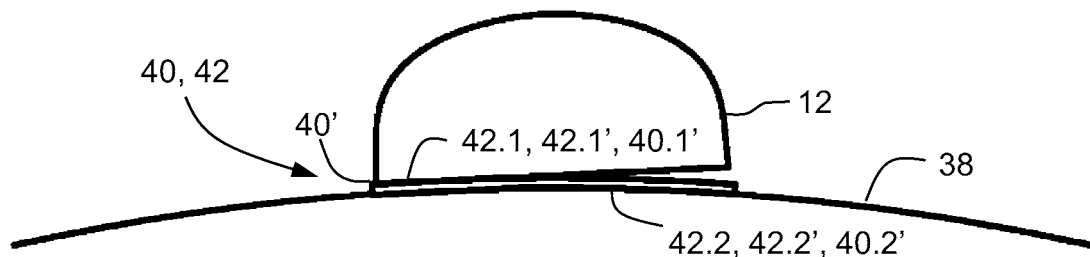
Figure 5F:
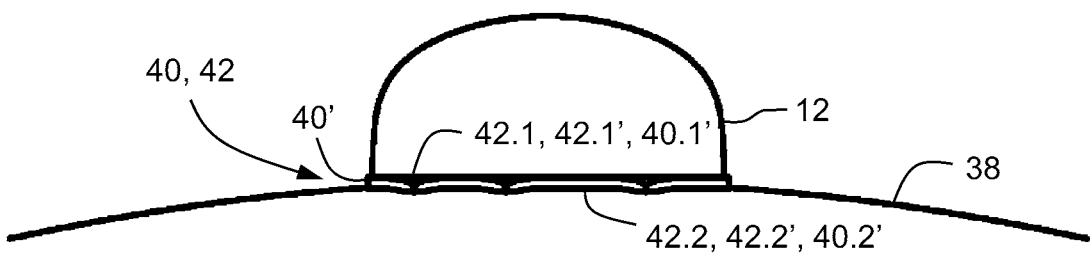
Figure 5G:
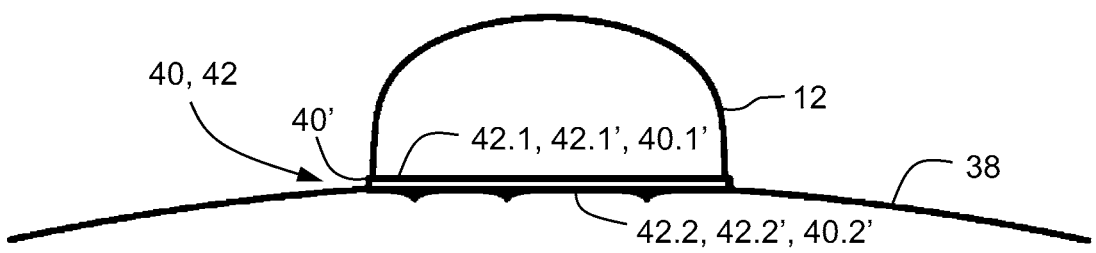

Referring also to FIG. 5a, the auscultatory sound sensors 12, $12^{1'}$, $12^{2'}$, $12^{3'}$, $12^{1''}$, $12^{2''}$, $12^{3''}$ are acoustically coupled to the skin 38 of the thorax 20 of the test-subject 22 via an acoustic interface 40, for example, via a hydrogel layer 40', that also functions as an associated adhesive interface 42 that is attached to the associated auscultatory sound sensor 12, $12^{1'}$, $12^{2'}$, $12^{3'}$, $12^{1''}$, $12^{2''}$, $12^{3''}$ with a first adhesive layer 42.1, for example, either a first surface 40.1' of the hydrogel layer 40' or a first layer of double-sided tape 42.1' on a first side of the acoustic/adhesive interface 40, 42, and that is attached to the skin 38 of the thorax 20 of the test-subject 22 with a second adhesive layer 42.2, for example, either a second surface 40.2' of the hydrogel layer 40' or a second layer of double-sided tape 42.2' on the opposing, second side of the acoustic/adhesive interface 40, 42. When fully coupled—as illustrated in FIG. 5a,—the auscultatory sound sensor 12, $12^{1'}$, $12^{2'}$, $12^{3'}$, $12^{1''}$, $12^{2''}$, $12^{3''}$ is fully attached to the acoustic/adhesive interface 40, 42 via the first adhesive layer 42.1, 42.1', 40.1', and the acoustic/adhesive interface 40, 42 is fully attached to the skin 38 of the thorax 20 of the test-subject 22 via the second adhesive layer 42.2, 42.2', 40.2', so that sound signals from within the thorax 20 of the test-subject 22 can propagate otherwise unimpeded to the auscultatory sound sensor 12, $12^{1'}$, $12^{2'}$, $12^{3'}$, $12^{1''}$, $12^{2''}$, $12^{3''}$, thereby providing for a maximum achievable level of the corresponding associated auscultatory sound signals 16, and thereby improving the prospect of detecting an associated abnormal cardiovascular condition—if present—therefrom. Referring to FIGS. 5b and 5c—with the acoustic/adhesive interface 40, 42 respectively detached from the skin 38 or detached from the auscultatory sound sensor 12, respectively,—if the auscultatory sound sensor 12, $12^{1'}$, $12^{2'}$, $12^{3'}$, $12^{1''}$, $12^{2''}$, $12^{3''}$ is completely detached from the skin 38 of the thorax 20 of the test-subject 22, and thereby fully decoupled therefrom, the resulting auscultatory sound sensor 12, $12^{1'}$, $12^{2'}$, $12^{3'}$, $12^{1''}$, $12^{2''}$, $12^{3''}$ would be substantially non-responsive to sound signals from within the thorax 20 of the test-subject 22. Referring to FIGS. 5d to 5g, if the auscultatory sound sensor 12, $12^{1'}$, $12^{2'}$, $12^{3'}$, $12^{1''}$, $12^{2''}$, $12^{3''}$ is partially attached to the skin 38 of the thorax 20 of the test-subject 22, and thereby partially decoupled therefrom—i.e., in a condition referred to herein as being debonded therefrom—the resulting auscultatory sound sensor 12, $12^{1'}$, $12^{2'}$, $12^{3'}$, $12^{1''}$, $12^{2''}$, $12^{3''}$ would be only partially responsive to sound signals from within the thorax 20 of the test-subject 22, but not sufficiently responsive to provide for an associated auscultatory sound signal 16 of sufficient amplitude to provide for reliably detecting a prospective associated abnormal cardiovascular condition. More particularly, FIGS. 5d and 5e respectively illustrate an acoustic/adhesive interface 40, 42 partially detached from skin 38, and an acoustic/adhesive interface 40, 42 partially detached from an auscultatory sound sensor 12, respectively. Furthermore, FIG. 5f illustrates an auscultatory sound sensor 12 attached to a wrinkled acoustic/adhesive interface 40, 42, and FIG. 5g illustrates an acoustic/adhesive interface 40, 42 attached to wrinkled skin 38. In anticipation of prospective problems with nature of the attachment of the acoustic/adhesive interface 40, 42, the Data Recording Application (DRA) 14 is provided with a means—described more fully hereinbelow—for detecting if one or more auscultatory sound sensors 12, $12^{1'}$, $12^{2'}$, $12^{3'}$, $12^{1\prime\prime}$, $12^{2\prime\prime}$, $12^{3\prime\prime}$ is, or are, either detached or debonded from the skin 38 of the thorax 20 of the test-subject 22, so as to provide for excluding data from auscultatory sound sensors 12, $12^{1\prime}$, $12^{2\prime}$, $12^{3\prime}$, $12^{1\prime\prime}$, $12^{2\prime\prime}$, $12^{3\prime\prime}$ that are either detached or debonded, from the skin 38 of the thorax 20 of the test-subject 22 from being used to diagnose a prospective abnormal cardiovascular condition.

Generally, the adhesive interface 42 could comprise either a hydrogel layer 40', for example, P-DERM® Hydrogel; a silicone material, for example, a P-DERM® Silicone Gel Adhesive; an acrylic material, for example, a P-DERM® Acrylic Adhesive; a rubber material; a synthetic rubber material; a hydrocolloid material; or a double-sided tape, for example, with either rubber, acrylic or silicone adhesives.

Figure 6:
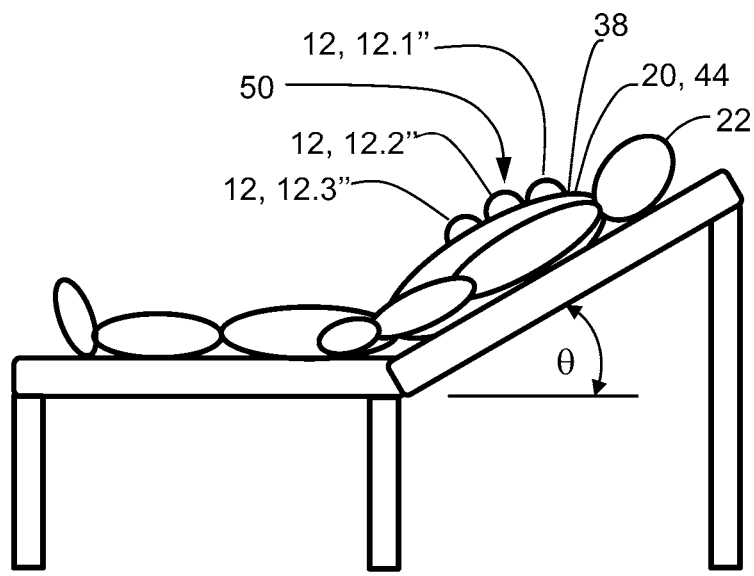
FIG. 6 illustrates a test-subject reclined on a surface, with their torso inclined while capturing auscultatory sound signals from a plurality of auscultatory sound sensors attached to the thorax of the test-subject.

Referring to FIG. 6, it has been found that the quality of the auscultatory sounds acquired from a test-subject 34 can be improved if the torso 44 of the test-subject 34 is inclined, for example, in one set of embodiments, at an inclination angle $\theta$ of about 30 degrees above horizontal—but generally, as close to upright (i.e. $\theta$=90 degrees) as can be accommodated by the associated adhesive interface(s) 42 of the associated auscultatory sound sensors 12, $12^{1\prime}$, $12^{2\prime}$, $12^{3\prime}$, $12^{1\prime\prime}$, $12^{2\prime\prime}$, $12^{3\prime\prime}$—which imposes a transverse component of gravitational force on each of the auscultatory sound sensors 12, $12^{1\prime}$, $12^{2\prime}$, $12^{3\prime}$, $12^{1\prime\prime}$, $12^{2\prime\prime}$, $12^{3\prime\prime}$ that is resisted by the associated adhesive interface(s) 42.

Referring to FIGS. 7-15, in accordance with a first aspect 700, an auscultatory-sound-sensing process 700 provides for first determining a scale factor SF from an initially-acquired block of auscultatory-sound-sensor time-series data S, and initially determining from the scale factor SF whether one or more of the auscultatory sound sensors 12, $12^{1\prime}$, $12^{2\prime}$, $12^{3\prime}$, $12^{1\prime\prime}$, $12^{2\prime\prime}$, $12^{3\prime\prime}$ is detached from the skin 38 of the thorax 20 of the test-subject 22, wherein when multiplied by the scale factor SF, the values of the associated auscultatory-sound-sensor time-series data S are nominally within a range that is a predetermined percentage of the dynamic range of the associated data acquisition system (for example, that provides 16-bit signed digital values). If there is no detachment, the first aspect 700, the auscultatory-sound-sensing process 700 provides for acquiring successive blocks of auscultatory-sound-sensor time-series data S while the test-subject 22 is holding their breath, and determining from each block of auscultatory-sound-sensor time-series data S—using an associated predetermined debond-detection threshold—whether or not one or more auscultatory sound sensors 12, $12^{1\prime}$, $12^{2\prime}$, $12^{3\prime}$, $12^{1\prime\prime}$, $12^{2\prime\prime}$, $12^{3\prime\prime}$ is debonded from the skin 38 of the thorax 20 of the test-subject 22, or whether there is excessive noise in the auscultatory-sound-sensor time-series data S. The auscultatory-sensor time-series data S is rejected if excessive noise is detected, and the test is aborted if one or more auscultatory sound sensors 12, $12^{1\prime}$, $12^{2\prime}$, $12^{3\prime}$, $12^{1\prime\prime}$, $12^{2\prime\prime}$, $12^{3\prime\prime}$ has become decoupled from the skin 38 of the thorax 20.

Figure 7:
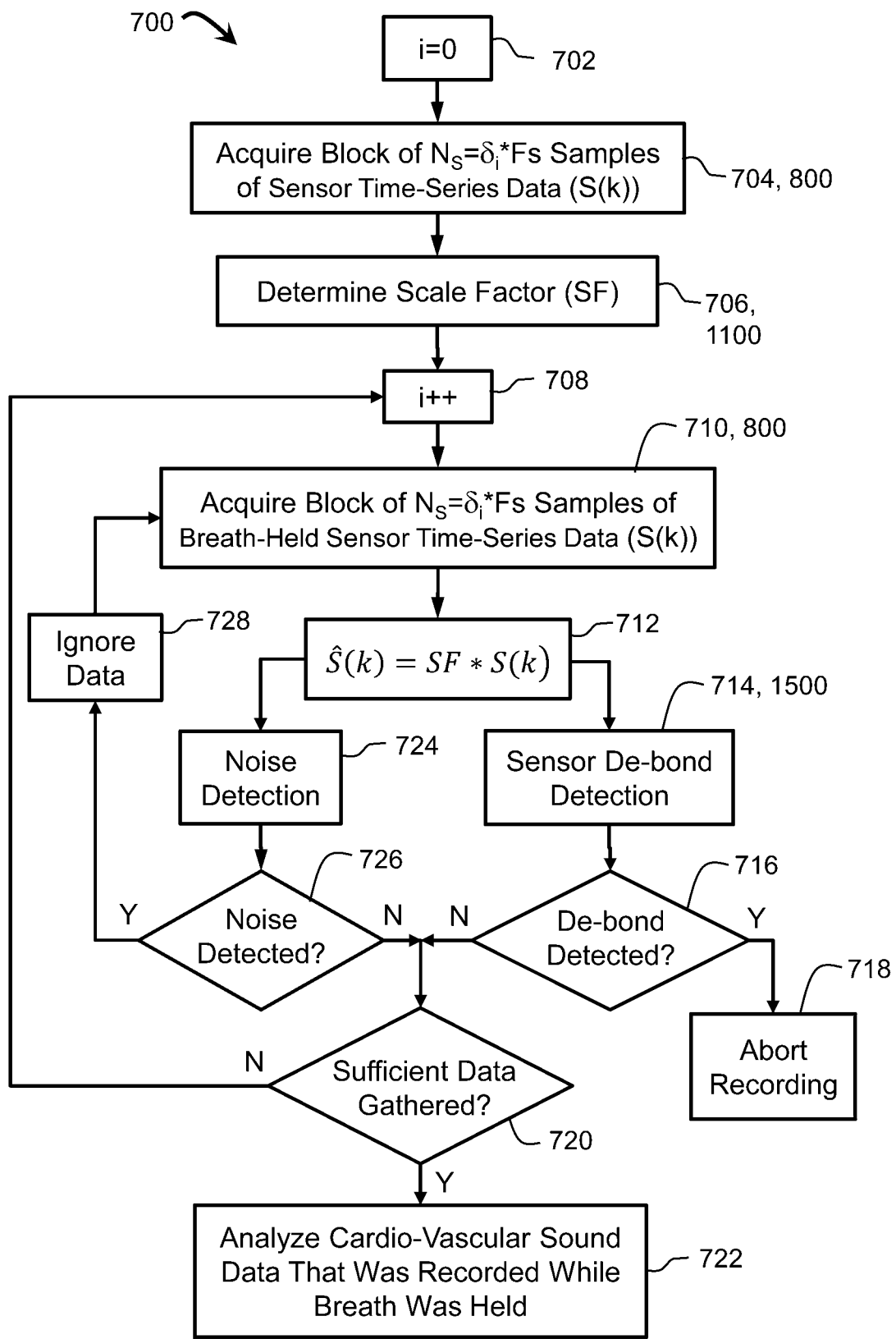
FIG. 7 illustrates a flowchart of a first aspect of an associated auscultatory-sound-sensing process that incorporates a process for detecting a decoupling of the associated auscultatory sound sensors from the skin of the thorax of a test-subject being diagnosed for a prospective abnormal cardiovascular condition, wherein the decoupling-detection process occurs after each block of breath-held auscultatory sound time-series data is acquired, and is based upon scaled time-series data and responsive to an associated pre-determined debond-detection threshold.

More particularly, referring to FIG. 7, the first aspect 700 of the auscultatory-sound-sensing process 700 commences with step (702) by initializing a data-block counter i to a value of zero, and then, in step (704), acquiring a block of Ns contiguous samples of auscultatory-sound-sensor time-series data S in accordance with a first aspect 800 of a data acquisition process 800. This initially-acquired data is then used to determine a scale factor SF that is used to determine whether or not one or more auscultatory sound sensors 12, $12^{1\prime}$, $12^{2\prime}$, $12^{3\prime}$, $12^{1\prime\prime}$, $12^{2\prime\prime}$, $12^{3\prime\prime}$ is/are detached from the skin 38 of the thorax 20 of the test-subject 22, and then subsequently to scale subsequent blocks of time-series data S. The initial block of auscultatory-sound-sensor time-series data S may be acquired either with, or without, the test-subject 22 holding their breath, but typically with the test-subject 22 allowed to breath normally—for their comfort and convenience. The number of samples $N_S$ to be acquired is given by the product of an acquisition period $\delta_i$ in seconds, times a sampling frequency Fs in Hz. For example, in one set of embodiments, in step (704), the initially-acquired block of auscultatory-sound-sensor time-series data S typically contains 10 seconds of data, which at a sampling frequency Fs of 24 KHz, results in $N_S=\delta_i*Fs=240,000$ samples.

Figure 8:
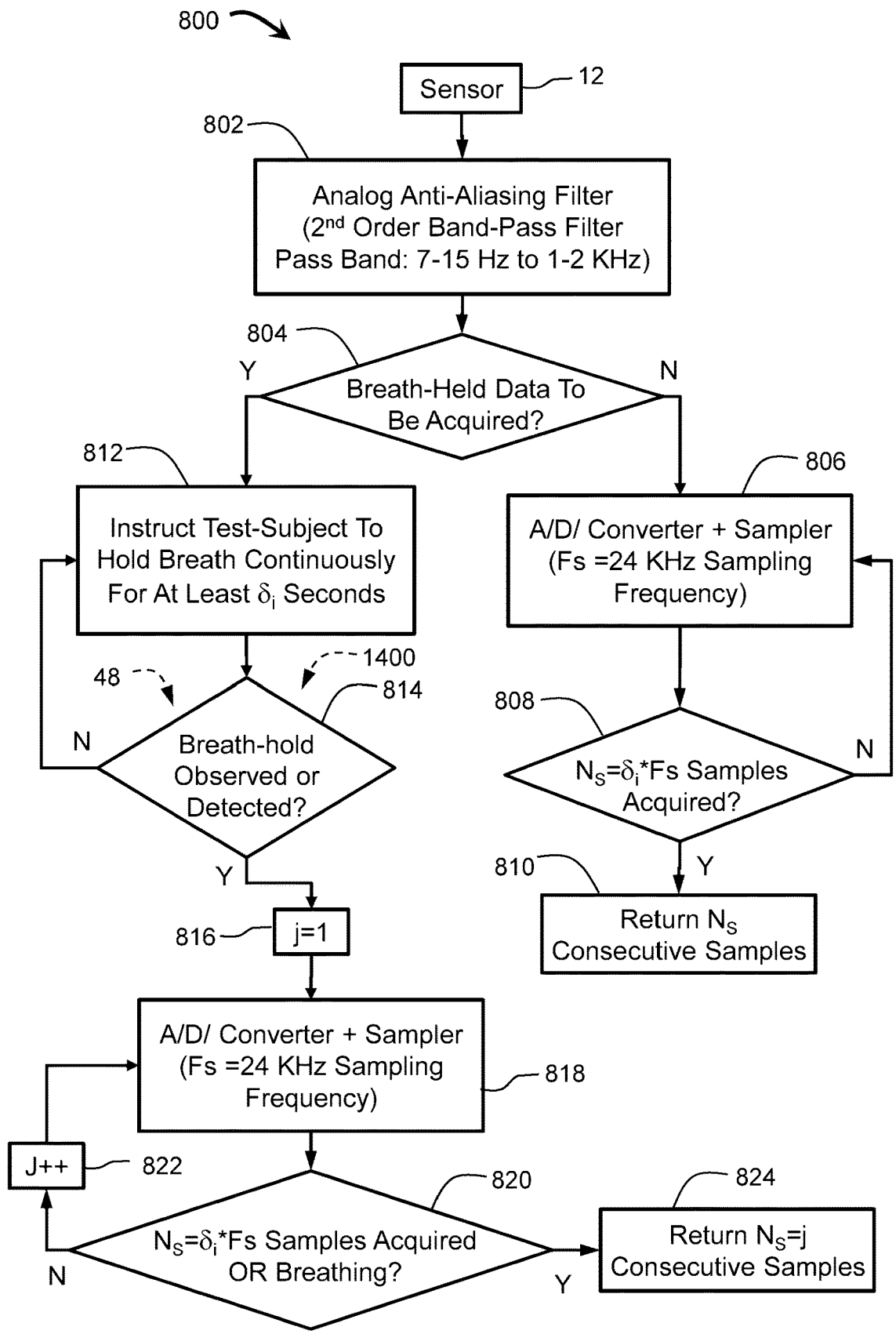
FIG. 8 illustrates a flowchart of a first aspect of a process for acquiring auscultatory sound signals from the associated auscultatory sound sensors coupled to the skin of the thorax of the test-subject being diagnosed for a prospective abnormal cardiovascular condition.

More particularly, referring to FIG. 8, the data acquisition process 800 commences with step (802) by pre-filtering the electronic signal from the associated auscultatory sound sensor 12, $12^{1\prime}$, $12^{2\prime}$, $12^{3\prime}$, $12^{1\prime\prime}$, $12^{2\prime\prime}$, $12^{3\prime\prime}$ with an analog anti-aliasing filter, for example, an analog second-order band-pass filter having a pass band in the range of 20 Hz to 1 KHz, for which the upper-cutoff frequency is sufficiently below the sampling frequency (i.e. no more than half) so as to prevent high frequency components in the signal being sampled from appearing as low frequency components of the sampled signal. Following step (802), if, in step (804), the test-subject 22 need not necessarily hold their breath—as is the case for the initially-acquired block of auscultatory-sound-sensor time-series data S,—then, in step (806), the pre-filtered auscultatory sound signal 16 is sampled at the sampling frequency Fs and converted to digital form by the associated analog-to-digital (ADC) converter. Then, from step (808), the auscultatory sound signal 16 continues to be sampled in step (806) until $N_S$ samples of the block of auscultatory-sound-sensor time-series data S have been acquired, after which, in step (810), the $N_S$ samples of auscultatory-sound-sensor time-series data S are returned to step (704) of the auscultatory-sound-sensing process 700. For example, FIGS. 9 and 10a each illustrate a first block of auscultatory-sound-sensor time-series data S of duration $\delta_0$ that was recorded from one of the auscultatory sound sensors 12, $12^{1\prime}$, $12^{2\prime}$, $12^{3\prime}$, $12^{1\prime\prime}$, $12^{2\prime\prime}$, $12^{3\prime\prime}$.

Referring again to FIG. 7, following step (704), in step (706), the scale factor SF is determined from the initially-acquired block of auscultatory-sound-sensor time-series data S, in accordance with an associated scale-factor-determination process 1100. More particularly, referring to FIGS. 11 and 12a, the scale-factor-determination process 1100 commences with step (1102), wherein the block of auscultatory-sound-sensor time-series data S is divided into a plurality of data segments 46, for example, each of the same data-segment duration $S_D$ that nominally spans a single heartbeat, for example, about one second. For example, in FIG. 12a, the $\delta_0$=10 second block of auscultatory-sound-sensor time-series data S is divided into $N_{seg}$=10 data segments 46, each of $S_D$=one second duration. FIG. 12a illustrates a time series |S| containing the absolute values of the auscultatory-sound-sensor time-series data S illustrated in FIG. 10a. As indicated by X's in FIG. 12a, for each data segment 46, m spanning the range $k=k_{MIN}(m)$ to $k=k_{MAX}(m)$ of the auscultatory-sound-sensor time-series data S(k), the corresponding maximum absolute value of the auscultatory-sound-sensor time-series data S(k) is determined, as given by:

$$S_m^{MAX} = \mathrm{MAX}(|S(k)|)_{k_{MIN}(m) \leq k \leq k_{MAX}(m)} \quad (1)$$

Then, in step (1104), the median of these maximum values is determined, as given by $$\mathrm{median}(S_{1 \leq m \leq N_{Seg}}^{MAX}) \quad (2)$$

Finally, in step (1106), the scale factor SF is determined, as given by:

$$SF = \frac{DR_{0-P}}{\text{median}(S_{1 \leq m \leq N_{Seg}}^{MAX})} \quad (3)$$

wherein $DR_{0-P}$ is the nominal zero-to-peak dynamic range of the auscultatory-sound-sensor time-series data S after scaling, i.e. after multiplying the acquired values by the scale factor SF. For example, in one set of embodiments, the nominal zero-to-peak dynamic range is set to be about 80 percent—more broadly, but not limiting, 80 percent plus or minus 15 percent—of the zero-to-peak range of the associated analog-to-digital converter—for example, in one set of embodiments, a 16-bit signed analog-to-digital converter—used to digitize the auscultatory-sound-sensor time-series data S in step (806). In one set of embodiments, the scale factor SF is integer-valued that, for an attached and bonded auscultatory sound sensor 12, 12$^{1\prime}$, 12$^{2\prime}$, 12$^{3\prime}$, 12$^{1\prime\prime}$, 12$^{2\prime\prime}$, 12$^{3\prime\prime}$, ranges in value between 1 and 28.

If one or more of the associated auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ is detached from the skin 38 of the thorax 20 of the test-subject 22, then the associated level of the auscultatory sound signals 16 will be low—for example, at a noise level—resulting in a relatively large associated scale factor SF from step (1106). Accordingly, if, in step (1108), the scale factor SF is in excess of an associated threshold $SF_{MAX}$, then the Data Recording Application (DRA) 14 is aborted in step (1110), and the operator 48 is alerted that the one or more auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ is/are detached, so that this can be remedied. For example, in one set of embodiments, the value of the threshold $SF_{MAX}$ is 28 for the above-described fixed-gain embodiment, i.e. for which the associated amplifier has a fixed gain of 88, feeding a 16-bit analog-to-digital converter (ADC) that provides for converting a +/−5 volt input signal to +/−32,767. Otherwise, from step (1108), if the value of the scale factor SF does not exceed the associated threshold $SF_{MAX}$, in step (1112), the scale factor SF is returned to step (706) for use in scaling subsequently-recorded breath-held auscultatory sound signals 16.1.

Referring again to FIG. 7, following step (706), in step (708), the value of the data-block counter i is incremented, so as to point to the next block of auscultatory-sound-sensor time-series data S to be recorded. If, while this next block is recorded, the auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ remain attached and bonded to the skin 38 of the thorax 20 of the test-subject 22, and the associated breath-held auscultatory sound signals 16.1 are not corrupted by excessive noise, then this next block of auscultatory-sound-sensor time-series data S will then be subsequently used to detect a prospective abnormal cardiovascular condition therefrom. The auscultatory sound signals 16 used to detect prospective abnormal cardiovascular conditions are recorded while the test-subject 22 holds their breath, the latter to prevent the resulting cardiovascular-based auscultatory sound signals 16 from being overwhelmed by breathing-related sounds that are substantially louder than cardiovascular-based sounds, thereby providing for improving the associated signal-to-noise ratio of the cardiovascular-based auscultatory sound signals 16.

Accordingly, in step (710), a next block of $N_S$ contiguous samples of auscultatory-sound-sensor time-series data S is acquired over an acquisition period b in accordance with a first aspect 800 of a data acquisition process 800, during which time the test-subject 22 is instructed to hold their breath. For example, in one set of embodiments, the nominal sampling period $\delta_i$ is 10 seconds—but at least 5 seconds,—which, at a sampling frequency Fs of 24 KHz, results in $N_S = \delta_i * Fs = 240{,}000$ samples.

More particularly, referring again to FIG. 8, the data acquisition process 800 commences with step (802) by pre-filtering the electronic signal from the associated auscultatory sound sensor 12, 12$^{1\prime}$, 12$^{2\prime}$, 12$^3$, 12$^{1\prime\prime}$, 12$^{2\prime\prime}$, 12$^{3\prime\prime}$ with the above-described analog anti-aliasing filter. Then, from step (804), because breath-held data is to be acquired, in step (812), the test-subject 22 is instructed by the operator 48 to hold their breath. In step (814), if the operator 48 observes that the test-subject 22 is compliant in holding their breath, or, additionally or alternatively, if this is confirmed by a below-described breath-hold detection process 1400, then upon manual initiation by the operator 48, in step (816), a sample counter j is initialized to a value of one, and, in step (818), the next sample of pre-filtered auscultatory sound signal 16 is sampled at the sampling frequency Fs and converted to digital form by an associated analog-to-digital (ADC) converter. This process continues until either $N_S = \delta_i * Fs$ samples have been acquired, or the test-subject 22 resumes breathing. More particularly, in step (820), if one or more addition samples remain to be acquired, and if the operator 48 continues to observe that the test-subject 22 is holding their breath, or, additionally or alternatively, if this is confirmed by a below-described breath-hold detection process 1400, then, in step (822) the sample counter j is incremented, and the next sample is acquired in step (818). Otherwise, from step (820), if either all $N_S = \delta_i * Fs$ samples have been acquired, or if either the operator 48 observes that the test-subject 22 has resumed breathing, or, additionally or alternatively, if this is confirmed by a below-described breath-hold detection process 1400, or, if the test-subject 22 indicates by their own separate manual switch input that they will resume breathing, then, in step (824), the data acquisition process 800 terminates, and the block of breath-held auscultatory-sound-sensor time-series data S containing $N_S = j$ samples is returned to step (710). In one set of embodiments, if, following step (814), the test-subject 22 is not holding their breath, the pre-filtered auscultatory sound signals 16 are also separately-recorded while waiting for the test-subject 22 to hold their breath, or resume doing so. In practice, the auscultatory sound signals 16 typically continue to be recorded between breath-held segments, that latter of which are identified by associated recorded start and stop times with respect to the associated continuous recording.

Figure 4:
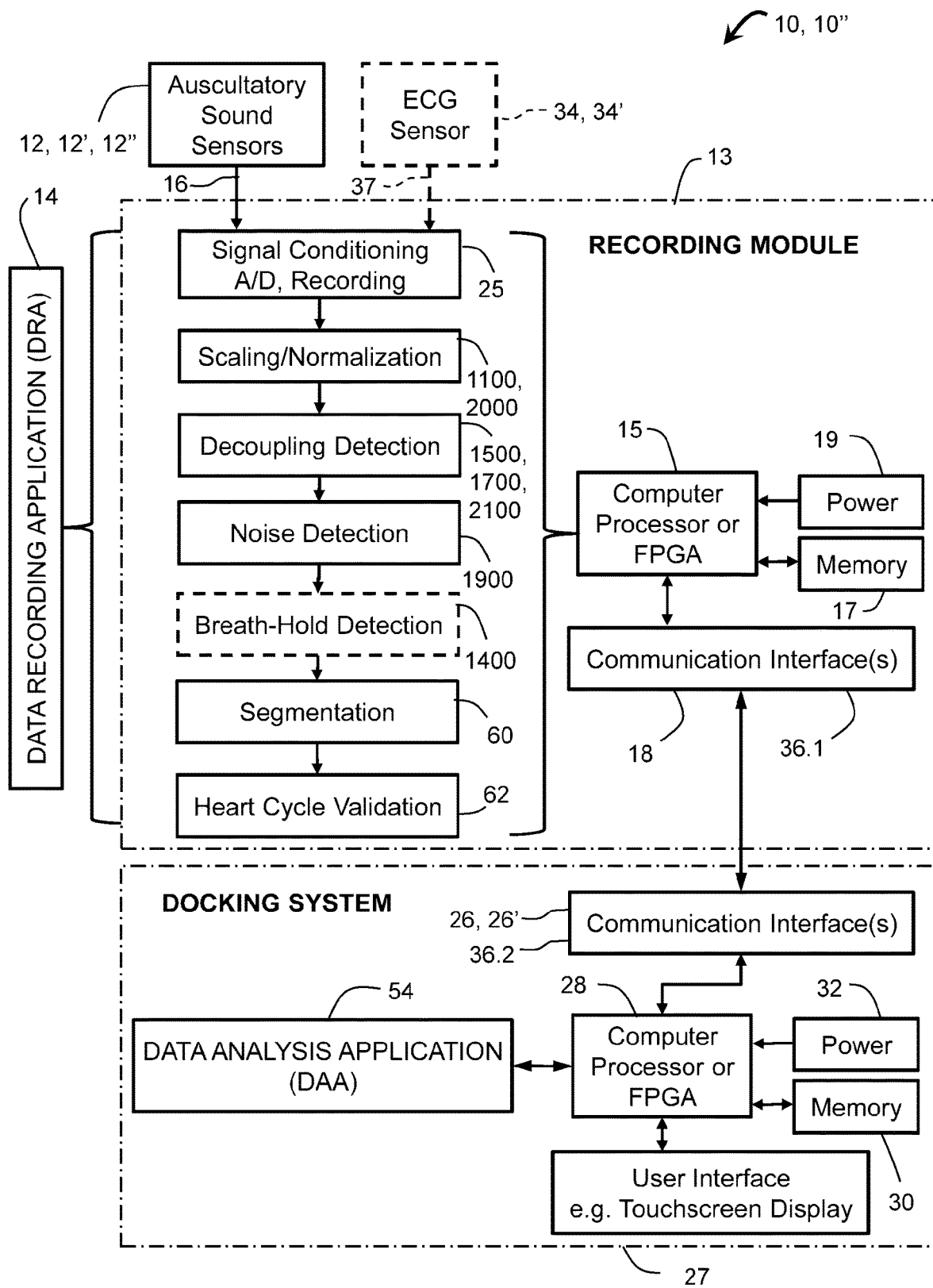
FIG. 4 illustrates a second aspect of a data recording module and a second aspect of an associated docking system, in accordance with a second aspect of the coronary-artery-disease detection system illustrated in FIG. 1.
Figure 13:
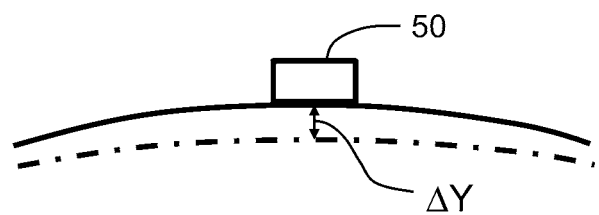
FIG. 13 illustrates an accelerometer on the thorax of a test-subject during a respiration cycle of the test-subject.

Referring also to FIG. 13, alternatively, or additionally, in step (814), the auscultatory coronary-artery-disease detection system 10 may further incorporate an accelerometer 50 operatively coupled to the thorax 20 of the test-subject 22 to provide an associated acceleration signal responsive to the motion of the thorax 20. With the test-subject 22 lying on their back at an inclined angle, for example, at about 30 degrees above horizontal, for example, as illustrated in FIG. 4 of U.S. Provisional Application No. 62/568,155 filed on 4 Oct. 2017, entitled AUSCULTATORY SOUND SENSOR, which has been incorporated by reference herein in its entirety, the associated acceleration signal—operatively coupled to recording module 13 and possibly transmitted to the docking system 27—may be twice integrated either in recording module 13 or the docking system 27 to generate a measure of the peak-to-peak displacement of the thorax 20, which if greater than a threshold would be indicative of breathing by the test-subject 22.

Figure 14:
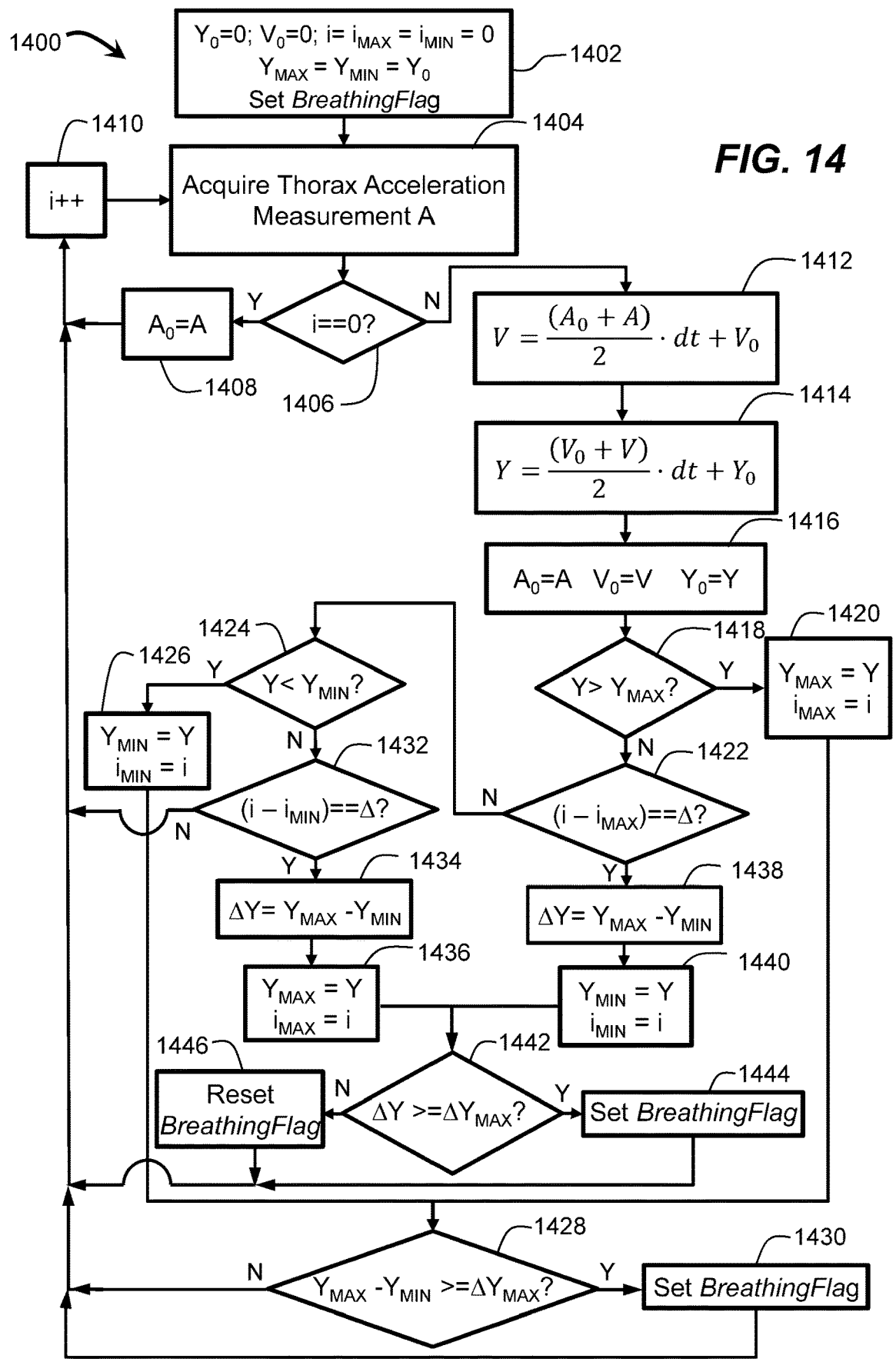
FIG. 14 illustrates a breath-hold detection process.

More particularly, referring also to FIG. 14, for an auscultatory coronary-artery-disease detection system 10 incorporating an accelerometer 50 operatively coupled to the thorax 20 of the test-subject 22, an acceleration signal 52 therefrom may alternatively or additionally be processed by an associated breath-hold detection process 1400 to provide for automatically determining—for example, in step (814) of the data acquisition process 800 illustrated in FIG. 8—whether or not the test-subject 22 is breathing, responsive to the determination, from the acceleration signal 52, of a peak-to-peak displacement of the thorax 20 of the test-subject 22. More particularly, beginning with, and in, step (1402), the respective previous/initial values of thorax displacement $Y_0$ and thorax velocity $V_0$, respectively, are each initialized to values of zero; a sample counter i is initialized to an initial value, for example, zero; the respective minimum $Y_{MIN}$ and maximum $Y_{MAX}$ values of thorax displacement are each set equal to the (initial) value of thorax displacement $Y_0$; the values of the sample counter $i_{MIN}$ and $i_{MAX}$ at which the corresponding minimum $Y_{MIN}$ and maximum $Y_{MAX}$ values of thorax displacement occur are set equal to the initial value of the sample counter i; and a BreathingFlag is set to indicate that the test-subject 22 is breathing. Then, in step (1404), the current sample of thorax acceleration A is acquired. Then, in step (1406), if the sample counter i is equal to the initial value, i.e. i=0, then, in step (1408), the previous value of thorax acceleration $A_0$ (i.e. initially, the initial value thereof) is set equal to the value of the current sample of thorax acceleration A, i.e. $A_0$=A, and then, in step (1410), the sample counter i is incremented, after which the breath-hold detection process 1400 repeats with step (1404).

Otherwise, from step (1406), if the current sample of thorax acceleration A is not the first sample, then, in step (1412), the current value of thorax velocity V is calculated by integrating the previous $A_0$ and current A measurements of thorax acceleration, for example, using a trapezoidal rule, as follows:

$$V = \frac{(A_0 + A)}{2} \cdot dt + V_0$$

wherein dt is the time period between samples in step (1404). Then, in step (1414), the current value of thorax displacement Y is calculated by integrating the above-calculated previous $V_0$ and current V values of thorax velocity, for example, again using a trapezoidal rule, as follows:

$$Y = \frac{(V_0 + V)}{2} \cdot dt + Y_0$$

Then, in step (1416), the respective previous values of thorax acceleration $A_0$, thorax displacement $Y_0$ and thorax velocity $V_0$ are respectively set equal to the corresponding current values of thorax acceleration A, thorax velocity V and thorax displacement Y, respectively, that will each be used in subsequent iterations of steps (1412) and (1414).

Then, in step (1418), if the current value of thorax displacement Y is greater than then current maximum value of thorax displacement $Y_{MAX}$—for example, as would result during a phase of chest expansion by the test-subject 22,—then, in step (1420), the current maximum value of thorax displacement $Y_{MAX}$ is set equal to the current value of thorax displacement Y and the corresponding value of the sample counter $i_{MAX}$ associated therewith is set to the current value of the sample counter i. Otherwise, from step (1418)—for example, as would result from other than a phase of chest expansion by the test-subject 22,—if, in step (1422), the amount by which the current value of the sample counter i exceeds the value of the sample counter $i_{MAX}$ associated with the maximum value of thorax displacement $Y_{MAX}$ is not equal to a threshold value Δ (the relevance of which is described more fully hereinbelow), then in step (1424), if the current value of thorax displacement Y is less than then current minimum value of thorax displacement $Y_{MIN}$—for example, as would result during a phase of chest contraction by the test-subject 22,—then, in step (1426), the current minimum value of thorax displacement $Y_{MIN}$ is set equal to the current value of thorax displacement Y and the corresponding value of the sample counter $i_{MIN}$ associated therewith is set to the current value of the sample counter i. From either steps (1420) or (1426), in step (1428), if the amount by which the current maximum value of thorax displacement $Y_{MAX}$ is greater the current minimum value of thorax displacement $Y_{MIN}$ meets or exceeds a displacement threshold $\Delta Y_{MAX}$, then, in step (1430), the BreathingFlag is set to indicate that the test-subject 22 is breathing, after which, in step (1410), the sample counter i is incremented, after which the breath-hold detection process 1400 repeats with step (1404). Similarly, from step (1428), if the displacement threshold $\Delta Y_{MAX}$ is not exceeded, in step (1410), the sample counter i is incremented, after which the breath-hold detection process 1400 repeats with step (1404). Further similarly, from step (1424)—for example, as would result from other than a phase of chest contraction by the test-subject 22,—if, in step (1432), the amount by which the current value of the sample counter i exceeds the value of the sample counter $i_{MIN}$ associated with the minimum value of thorax displacement $Y_{MIN}$ is not equal to the threshold value Δ, in step (1410), the sample counter i is incremented, after which the breath-hold detection process 1400 repeats with step (1404).

If, from step (1432), the amount by which the current value of the sample counter i exceeds the value of the sample counter $i_{MIN}$ associated with the minimum value of thorax displacement $Y_{MIN}$ is equal to the threshold value Δ—following a minimum chest contraction of the test-subject 22, in anticipation of subsequent chest expansion, wherein the threshold value Δ is greater than or equal to one,—then, in step (1434), the peak-to-peak thorax displacement ΔY is calculated as the difference between the current maximum $Y_{MAX}$ and minimum $Y_{MIN}$ values of thorax displacement, and, in step (1436), the maximum value of thorax displacement $Y_{MAX}$ is set equal to the current value of thorax displacement Y, and the value of the sample counter $i_{MAX}$ at which the corresponding maximum value of thorax displacement $Y_{MAX}$ occurred is set equal to the current value of the sample counter i, in anticipation of subsequently increasing magnitudes of the current value of thorax displacement Y to be tracked in steps (1418) and (1420).

Similarly, if, from step (1422), the amount by which the current value of the sample counter i exceeds the value of the sample counter $i_{MAX}$ associated with the maximum value of thorax displacement $Y_{MAX}$ is equal to the threshold value Δ—following a maximum chest expansion of the test-subject 22, in anticipation of subsequent chest contraction, wherein the threshold valued Δ is greater than or equal to one,—then, in step (1438), the peak-to-peak thorax displacement ΔY is calculated as the difference between the current maximum $Y_{MAX}$ and minimum $Y_{MIN}$ values of thorax displacement, and, in step (1440), the minimum value of thorax displacement $Y_{MIN}$ is set equal to the current value of thorax displacement Y, and the value of the sample counter $i_{MIN}$ at which the corresponding minimum value of thorax displacement $Y_{MIN}$ occurred is set equal to the current value of the sample counter i, in anticipation of subsequently decreasing magnitudes of the current value of thorax displacement Y to be tracked in steps (1424) and (1426).

From either steps (1436) or (1440), in step (1442), if the amount of the peak-to-peak thorax displacement ΔY calculated in steps (1434) or (1438), respectively, meets or exceeds the displacement threshold $\Delta Y_{MAX}$, then, in step (1444), the BreathingFlag is set to indicate that the test-subject 22 is breathing. Otherwise, from step (1442), if the amount of the peak-to-peak thorax displacement ΔY calculated in steps (1434) or (1438), respectively, does not exceed the displacement threshold $\Delta Y_{MAX}$, then, in step (1446), the BreathingFlag is reset to indicate that the test-subject 22 is not breathing. Following either step (1444) or (1446), in step (1410), the sample counter i is incremented, after which the breath-hold detection process 1400 repeats with step (1404).

Referring again to FIG. 7, in step (712), a corresponding block of scaled auscultatory-sound-sensor time-series data Ŝ is calculated by multiplying the acquired block of auscultatory-sound-sensor time-series data S by the scale factor SF, and in step (714), the scaled auscultatory-sound-sensor time-series data Ŝ is analyzed by an associated debond detection process 1500 to determine whether or not any of the auscultatory sound sensors 12, $12^{1\prime}$, $12^{2\prime}$, $12^{3\prime}$, $12^{1\prime\prime}$, $12^{2\prime\prime}$, $12^{3\prime\prime}$ was debonded from skin 38 of the thorax 20 of the test-subject 22 during the associated data acquisition process 800.

Figure 15:
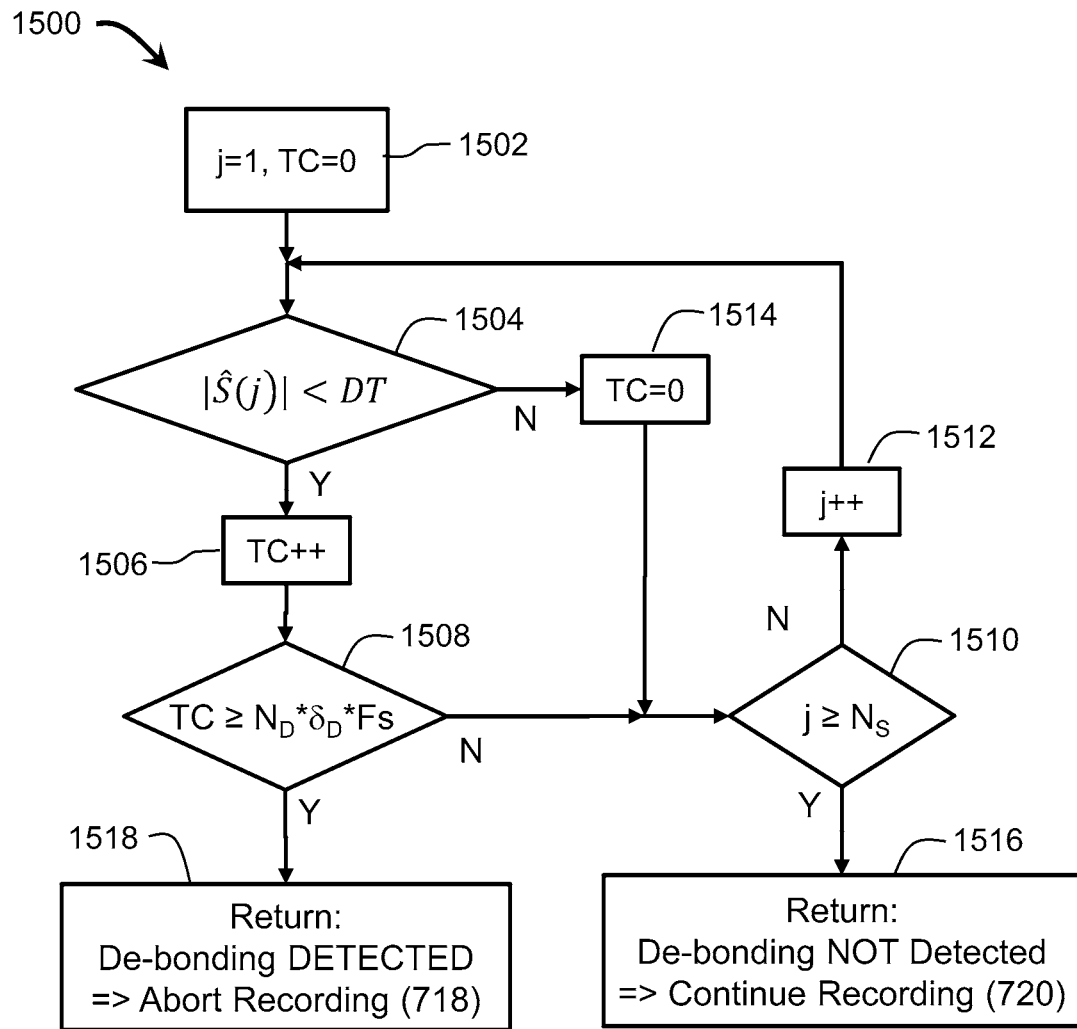
FIG. 15 illustrates a flowchart of a first aspect of a process for detecting whether or not an auscultatory sound sensor is debonded from the skin of a test-subject.

More particularly, referring to FIG. 15, the debond detection process 1500 commences with step (1502) by initializing a sample counter j to a value of one, and initializing a threshold counter TC to a value of zero, wherein the threshold counter TC is a count of the number of contiguous successive samples for which the value of the scaled auscultatory-sound-sensor time-series data Ŝ is less than an associated predetermined debond-detection threshold DT. For example, in one set of embodiments, the debond-detection threshold DT is set to a value that is about 20% of the achievable maximum value of the output from the analog-to-digital converter (ADC). Then, in step (1504), if the absolute value of the sample of scaled auscultatory-sound-sensor time-series data Ŝ, i.e. |Ŝ (j)|, is less than the predetermined debond-detection threshold DT (or, alternatively, if |SF*S(j)|<DT, thereby precluding a need to separately calculate and store scaled auscultatory-sound-sensor time-series data Ŝ), then in step (1506), the threshold counter TC is incremented, after which, in step (1508), if the value of the threshold counter TC does not exceed the number of samples in $N_D$ successive data segments 46, i.e. $TC < N_D * \delta_D * Fs$, and in step (1510), if the sample counter j does not exceed the number of samples $N_S$ in the block of scaled auscultatory-sound-sensor time-series data Ŝ, then, in step (1512), the sample counter j is incremented, and the process continues again with step (1504). Otherwise, from step (1504), if the absolute value of the current sample of scaled auscultatory-sound-sensor time-series data Ŝ, i.e. |Ŝ (j)|, is not less than the predetermined debond-detection threshold DT—indicating that the auscultatory sound sensor 12, $12^{1\prime}$, $12^{2\prime}$, $12^{3\prime}$, $12^{1\prime\prime}$, $12^{2\prime\prime}$, $12^{3\prime\prime}$ is not debonded from the skin 38 of the thorax 20 of the test-subject 22,—then, in step (1514), the threshold counter TC is reset to a value of zero and the process continues with step (1510). Otherwise, from step (1510), if the sample counter j exceeds the number of samples $N_S$ in the block of scaled auscultatory-sound-sensor time-series data Ŝ or auscultatory-sound-sensor time-series data S—indicating that the entire block of scaled auscultatory-sound-sensor time-series data Ŝ or auscultatory-sound-sensor time-series data S has been screened,—then the debond detection process 1500 is terminated with step (1516) by returning an indication to step (714) of the auscultatory-sound-sensing process 700 that the associated auscultatory sound sensor 12, $12^{1\prime}$, $12^{2\prime}$, $12^{3\prime}$, $12^{1\prime\prime}$, $12^{2\prime\prime}$, $12^{3\prime\prime}$ is not debonded from the skin 38 of the thorax 20 of the test-subject 22. Otherwise, from step (1508), if the value of the threshold counter TC exceeds the number of samples in $N_D$ successive data segments 46, then the debond detection process 1500 is terminated with step (1518) by returning an indication to step (714) of the auscultatory-sound-sensing process 700 that the associated auscultatory sound sensor 12, $12^{1\prime}$, $12^{2\prime}$, $12^{3\prime}$, $12^{1\prime\prime}$, $12^{2\prime\prime}$, $12^{3\prime\prime}$ is debonded from the skin 38 of the thorax 20 of the test-subject 22. For example, in one set of embodiments, the value of $N_D$ is equal to 4, and the value of $\delta_D$ is equal to 1 second.

Returning to FIG. 7, in step (716), if, from step (714), the debond detection process 1500 detected that the associated auscultatory sound sensor 12, $12^{1\prime}$, $12^{2\prime}$, $12^{3\prime}$, $12^{1\prime\prime}$, $12^{2\prime\prime}$, $12^{3\prime\prime}$ was debonded while acquiring the block of auscultatory-sound-sensor time-series data S, then the Data Recording Application (DRA) 14 is aborted in step (718), and the operator 48 is alerted that one or more auscultatory sound sensors 12, $12^{1\prime}$, $12^{2\prime}$, $12^{3\prime}$, $12^{1\prime\prime}$, $12^{2\prime\prime}$, $12^{3\prime\prime}$ are debonded, so that this can be remedied. Otherwise, if, from step (714), the debond detection process 1500 did not detect that the associated auscultatory sound sensor 12, $12^{1\prime}$, $12^{2\prime}$, $12^{3\prime}$, $12^{1\prime\prime}$, $12^{2\prime\prime}$, $12^{3\prime\prime}$ was debonded while acquiring the block of auscultatory-sound-sensor time-series data S, then, in step (720), if sufficient noise-screened data has not been gathered—for example, in one set of embodiments, a total duration of at least 65 seconds of recorded data,—then the auscultatory-sound-sensing process 700 continues with step (708).

In step (724), an associated noise detection (i.e. noise-screening) process—operating on either the block of scaled auscultatory-sound-sensor time-series data Ŝ, or the block of auscultatory-sensor time-series data S, in parallel with the debond detection process 1500—provides for detecting if the block of auscultatory-sound-sensor time-series data S has been corrupted by excessive noise, and if so, from step (726), that block of auscultatory-sound-sensor time-series data S is ignored, and the auscultatory-sound-sensing process 700 continues by repeating step (710) to acquire a new block of auscultatory-sound-sensor time-series data S. Otherwise, from step (726), if the block auscultatory-sound-sensor time-series data S has not been corrupted by excessive noise, the process continues with the above-described step (720).

From step (720), if sufficient noise-screened data has been gathered for which the associated one or more auscultatory sound sensors 12, $12^{1\prime}$, $12^{2\prime}$, $12^{3\prime}$, $12^{1\prime\prime}$, $12^{2\prime\prime}$, $12^{3\prime\prime}$ were not debonded from the skin 38 of the thorax 20 of the test-subject 22—for example, in one set of embodiments, a total duration of at least 65 seconds of recorded data,—then, in step (722), at least the composite set of blocks of breath-held auscultatory-sound-sensor time-series data S acquired in step (710) are subsequently analyzed by an associated Data Analysis Application (DAA) 54 operative on the docking system 27—as illustrated in FIGS. 2 and 3—so as to provide for detecting an abnormal cardiovascular condition of the test-subject 22. In addition to recording the segments of breath-held data, alternatively, all data may be recorded and provided to the Data Analysis Application (DAA) 54, along with an associated index that provides for identifying the corresponding associated breath-held portions thereof for which the associated auscultatory sound sensors 12, $12^{1\prime}$, $12^{2\prime}$, $12^{3\prime}$, $12^{1\prime\prime\prime}$, $12^{2\prime\prime\prime}$, $12^{3\prime\prime\prime}$ were neither detached nor debonded from the skin 38 of the thorax 20 of the test-subject 22, nor corrupted by noise.

Figure 10B:
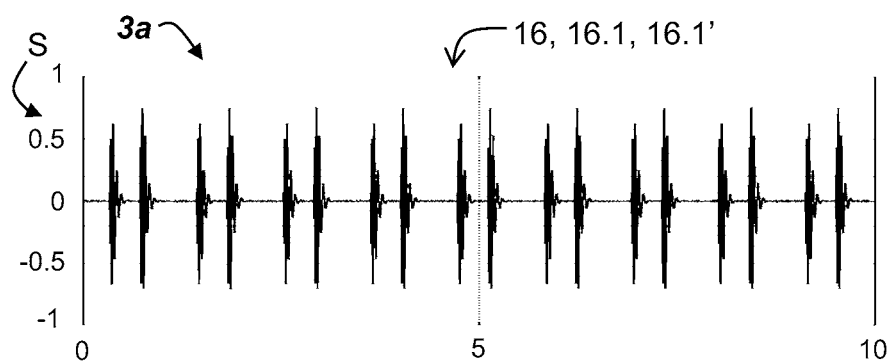
Figure 12B:
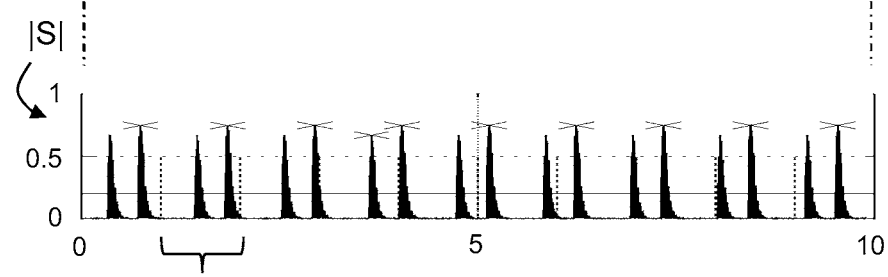
Figure 10C:
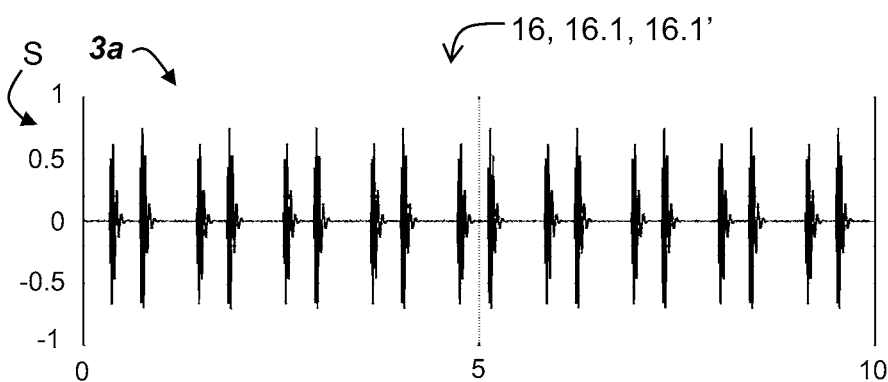
Figure 12C:
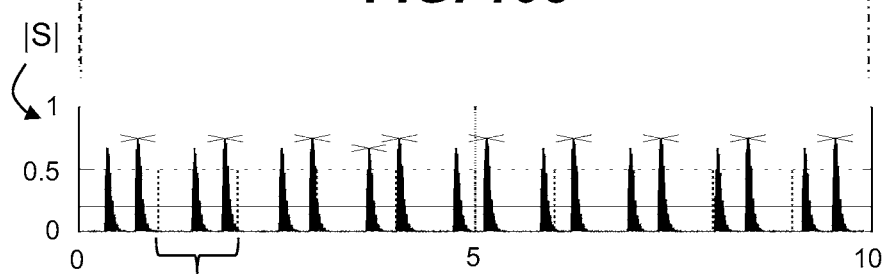
Figure 10D:
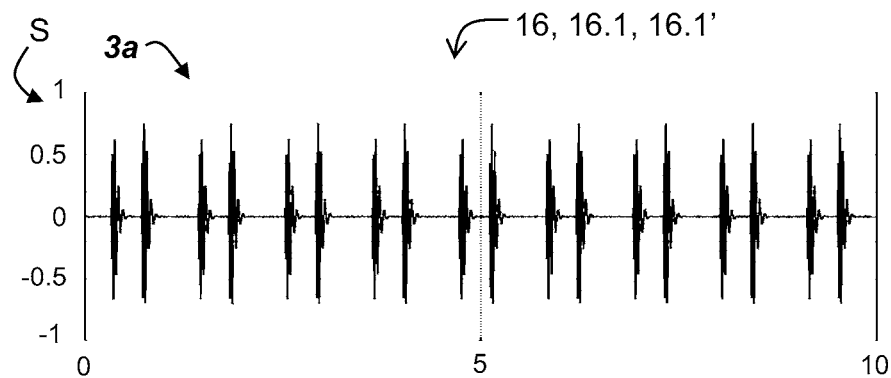
Figure 12D:
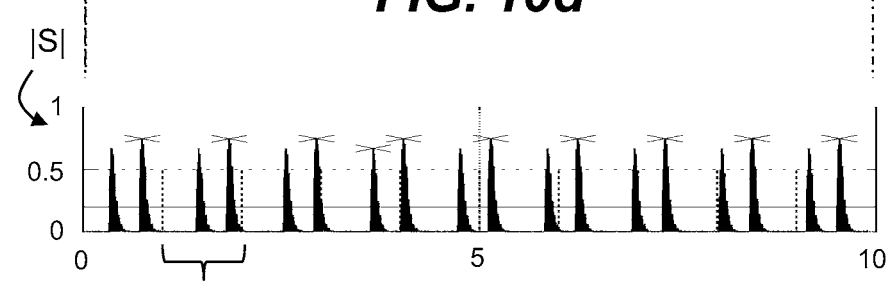
Figure 10E:
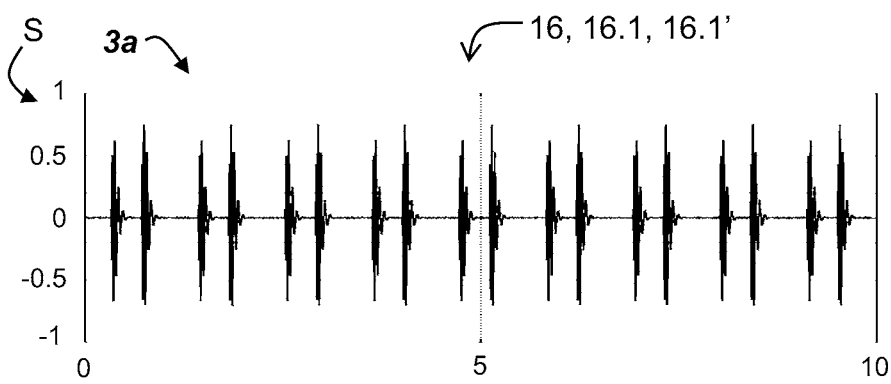
Figure 12E:
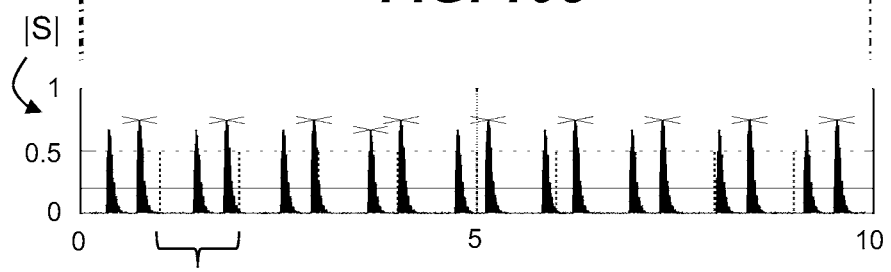

FIGS. 9 and 10a-10f illustrate a simulation of six blocks of breath-held auscultatory-sound-sensor time-series data S recorded in accordance with the first aspect 700 of auscultatory-sound-sensing process 700, with respective durations of $\delta_1$, $\delta_2$, $\delta_3$, $\delta_4$, $\delta_5$, and $\delta_6$ during which time periods the test-subject 22 was holding their breath, separated by periods $\Delta_1$, $\Delta_2$, $\Delta_3$, $\delta_4$, and $\delta_5$ of normal breathing, wherein FIGS. 10a-10e illustrate breath-held auscultatory sound signals 16.1, 16.1' from a normally-bonded auscultatory sound sensor 12, $12^{1\prime}$, $12^{2\prime}$, $12^{3\prime}$, $12^{1\prime\prime\prime}$, $12^{2\prime\prime\prime}$, $12^{3\prime\prime\prime}$ as illustrated in FIG. 5a, and FIG. 10f illustrates a breath-held auscultatory sound signal 16.1, 16.1" from a debonded auscultatory sound sensor 12, $12^{1\prime}$, $12^{2\prime}$, $12^{3\prime}$, $12^{1\prime\prime\prime}$, $12^{2\prime\prime\prime}$, $12^{3\prime\prime\prime}$, for example, as illustrated in any of FIGS. 5d-5g, for example, as might be caused by excessive hair between the adhesive interface 40 and the auscultatory sound sensor 12, poor placement of the auscultatory sound sensor 12 on the thorax 20 of the test-subject 22, poor angular orientation of the auscultatory sound sensor 12 relative to the surface of the skin 38, or wrinkled adhesive interface 40 between the auscultatory sound sensor 12 and the skin 38, For purposes of simplicity of illustration, FIGS. 10b-10e are identical to FIG. 10a. However, it should be understood that typically the amplitude of the auscultatory sound signals 16, 16.1 varies from heartbeat to heartbeat, and from one breath-held segment to another.

Figure 16:
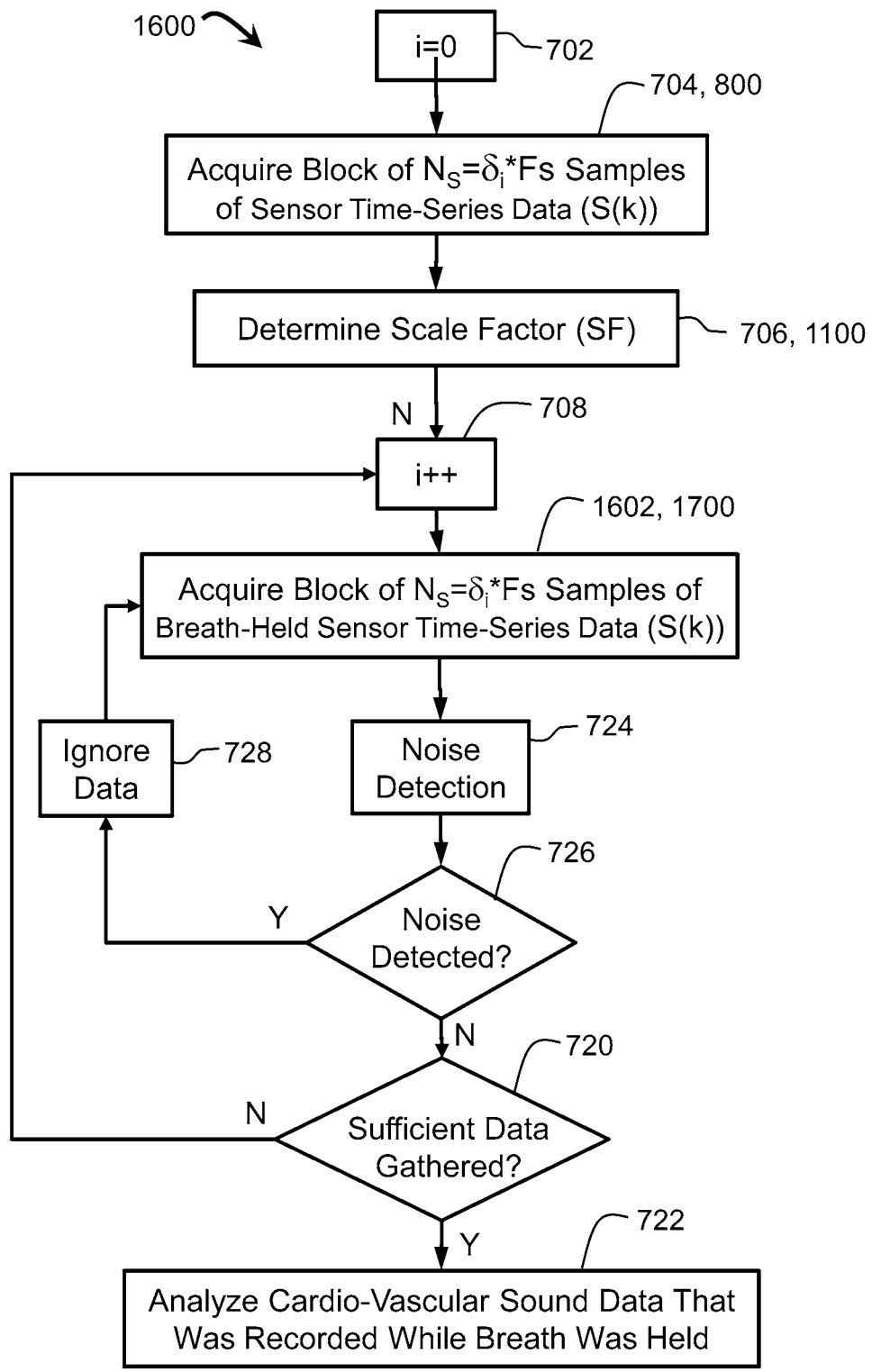
FIG. 16 illustrates a flowchart of a second aspect of an associated auscultatory-sound-sensing process that incorporates a process for detecting a decoupling of the associated auscultatory sound sensors from skin of the thorax of the test-subject, wherein the decoupling-detection process occurs concurrently with the associated data acquisition process.
Figure 17:
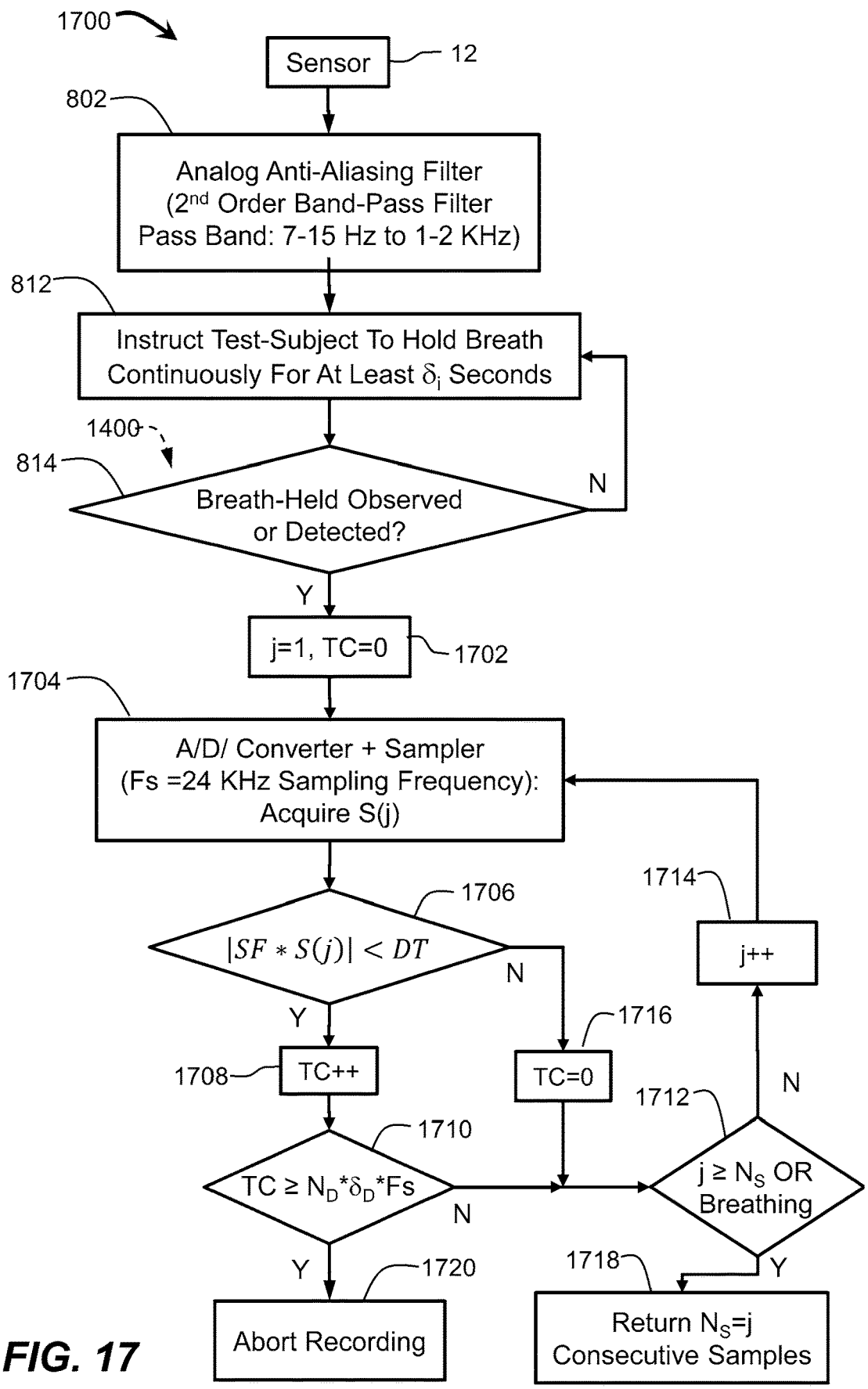
FIG. 17 illustrates a flowchart of a second aspect of a process for acquiring auscultatory sound signals from the associated auscultatory sound sensors coupled to the skin of the thorax of the test-subject, and an associated second aspect of a process for detecting whether or not an auscultatory sound sensor is debonded from the skin of the test-subject, in accordance with the second aspect of the associated auscultatory-sound-sensing process.

Referring to FIGS. 16 and 17, a second aspect 1600 of an auscultatory-sound-sensing process 1600 is substantially the same as the first aspect 700, except that the process of determining whether or not one or more auscultatory sound sensors 12, $12^{1\prime}$, $12^{2\prime}$, $12^{3\prime}$, $12^{1\prime\prime\prime}$, $12^{2\prime\prime\prime}$, $12^{3\prime\prime\prime}$ is debonded from the skin 38 of the thorax 20 of the test-subject 22 occurs while—rather than after—the auscultatory sound signals 16 are acquired, for each associated block of auscultatory-sound-sensor time-series data S.

More particularly, referring to FIG. 16, the second aspect 1600 of the auscultatory-sound-sensing process 1600 is the same as the first aspect 700 illustrated in FIG. 7, except that step (710) of the first aspect 700, calling the first aspect 800 of the data acquisition process 800, is replaced with step (1602), which in turn calls a second aspect 1700 of a data acquisition process 1700, the latter of which supersedes steps (712), (714), (716) and (718) of the first aspect 700 of the auscultatory-sound-sensing process 700.

More particularly, referring to FIG. 17, the second aspect 1700 of the data acquisition process 1700 commences with steps (802), (812) and (814), which are the same as the like-numbered, above-described steps of the first aspect 800 of the data acquisition process 800 illustrated in FIG. 8. In step (814), if the operator 48 observes that the test-subject 22 is compliant in holding their breath or, additionally or alternatively, if this is confirmed by the above-described breath-hold detection process 1400 illustrated in FIG. 14, then upon manual initiation by the operator 48, in step (1702), a sample counter j is initialized to a value of one, and a threshold counter TC is initialized to a value of zero, wherein the sample counter j and the threshold counter TC have the same functions as described hereinabove in respect of the first aspect 1500 of the debond detection process 1500. Then, in step (1704), the next sample of the pre-filtered auscultatory sound signal 16 is sampled at the sampling frequency Fs and converted to digital form by the associated analog-to-digital (ADC) converter.

Then, in step (1706), if the absolute value of the product of the predetermined scale factor SF times the currently-acquired value of the auscultatory-sound-sensor time-series data S(j) is less than the predetermined debond-detection threshold DT, i.e. $|SF*S(j)|<DT$, then in step (1708), the threshold counter TC is incremented, after which, in step (1710), if the value of the threshold counter TC does not exceed the number of samples in $N_D$ successive data segments 46, i.e. $TC<N_D*\delta_D*Fs$, and in step (1712), if the sample counter j does not exceed the number of samples $N_S$ to be acquired in the block of auscultatory-sound-sensor time-series data S, then, in step (1714), the sample counter j is incremented, and the data-acquisition process continues again with step (1704). Otherwise, from step (1706), if the absolute value of the product of the scale factor SF times the currently-acquired value of the auscultatory-sound-sensor time-series data S(j) does not exceed the predetermined debond-detection threshold DT, i.e. $|SF*S(j)|\geq DT$,—indicating that the auscultatory sound sensor 12, $12^{1\prime}$, $12^{2\prime}$, $12^{3\prime}$, $12^{1\prime\prime\prime}$, $12^{2\prime\prime\prime}$, $12^{3\prime\prime\prime}$ is not debonded from the skin 38 of the thorax 20 of the test-subject 22, then, in step (1716), the threshold counter TC is reset to a value of zero and the process continues with above-described step (1712). Otherwise, from step (1712), if the sample counter j is greater than or equal to the number of samples $N_S$ to be acquired in the block of auscultatory-sound-sensor time-series data S—indicating that the entire block of auscultatory-sound-sensor time-series data S has been acquired and screened,—or if the operator 48 observes, the breath-hold detection process 1400 detects, or the test-subject 22 signals, that the test-subject 22 is no longer holding their breath, then the data acquisition process 1700 terminates with step (1718) by returning the block of auscultatory-sound-sensor time-series data S. Otherwise, from step (1710), if the value of the threshold counter TC exceeds the number of samples in $N_D$ successive data segments 46, then the Data Recording Application (DRA) 14 is aborted in step (1720), and the operator 48 is alerted that one or more auscultatory sound sensors 12, $12^{1\prime}$, $12^{2\prime}$, $12^{3\prime}$, $12^{1\prime\prime\prime}$, $12^{2\prime\prime\prime}$, $12^{3\prime\prime\prime}$ are debonded, so that this can be remedied.

Returning to FIG. 16, following step (1602), the second aspect 1600 of the auscultatory-sound-sensing process 1600 continues with above-described step (724), i.e. with the associated noise detection process, but operating on the block of auscultatory-sound-sensor time-series data S. If, from step (724), the block of auscultatory-sound-sensor time-series data S has been found to have been corrupted by excessive noise, then, from step (726), that block of auscultatory-sound-sensor time-series data S is ignored, and the auscultatory-sound-sensing process 1600 continues by repeating step (1602) to acquire a new block of auscultatory-sound-sensor time-series data S. Otherwise, from step (726), if the block auscultatory-sound-sensor time-series data S has not been corrupted by excessive noise, the process continues with above-described step (720), the same as in the first aspect 700 of the auscultatory-sound-sensing process 700.

Figure 18:
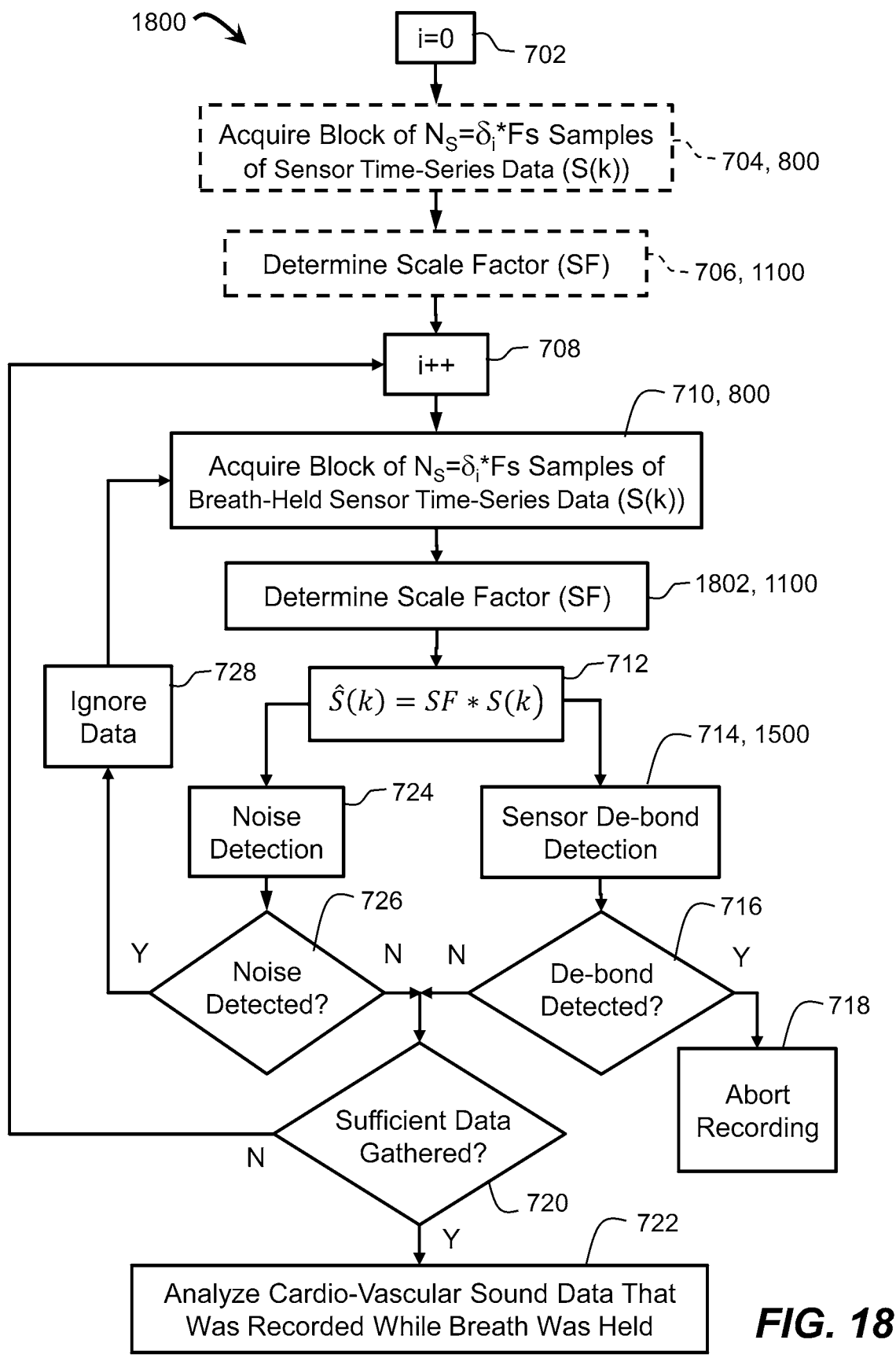
FIG. 18 illustrates a flowchart of a third aspect of an associated auscultatory-sound-sensing process that incorporates a process for detecting a decoupling of the associated auscultatory sound sensors from skin of the thorax of the test-subject, wherein a separate scale factor is determined for each block of breath-held auscultatory sound time-series data, and the decoupling-detection process occurs after each block of breath-held auscultatory sound time-series data is acquired.

Referring to FIG. 18, a third aspect 1800 of an auscultatory-sound-sensing process 1800 is substantially the same as the first aspect 700, except that a separate scale factor SF is determined for each block of auscultatory-sound-sensor time-series data S. More particularly, the third aspect 1800 of the auscultatory-sound-sensing process 1800 is the same as the first aspect 700 illustrated in FIG. 7, except that following the acquisition of each block of auscultatory-sound-sensor time-series data S in step (710), in step (1802), a new scale factor SF is determined in accordance with the above-described scale-factor-determination process 1100 prior to the determination of the scaled auscultatory-sound-sensor time-series data Ŝ in step (712). Furthermore, given that the scale factor SF is determined for each new block of auscultatory-sound-sensor time-series data S, steps (704) and (706)—which provide for initially acquiring the block of auscultatory-sound-sensor time-series data S for which the test-subject 22 need not hold their breath, and then calculating the associated scale factor SF therefrom—are optional, although would still have utility in providing for an initial determination of whether or not one or more auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ is/are detached from the skin 38 of the thorax 20 of the test-subject 22, without requiring the test-subject 22 to hold their breath.

Figure 19:
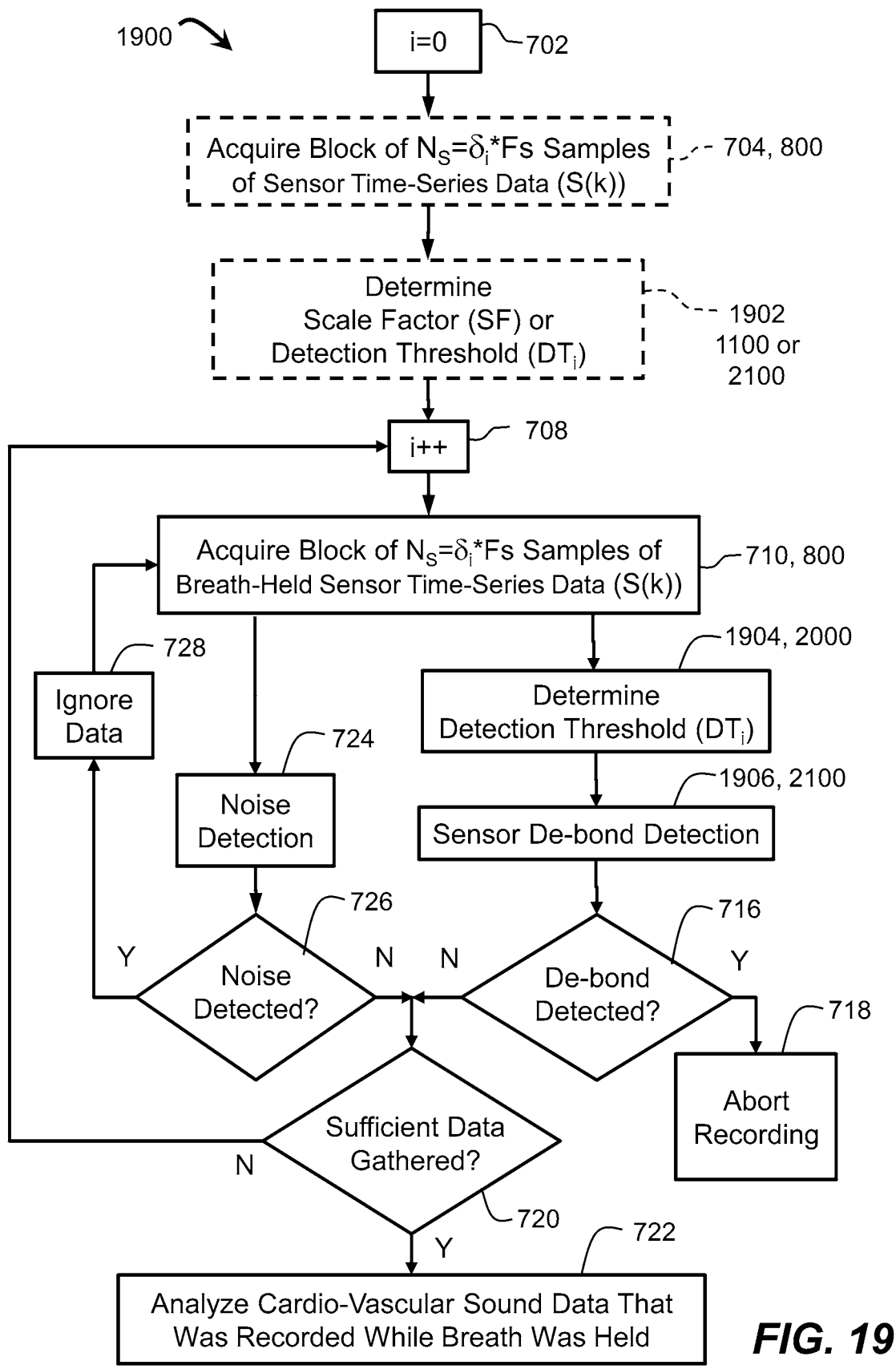
FIG. 19 illustrates a flowchart of a fourth aspect of an associated auscultatory-sound-sensing process that incorporates a process for detecting a decoupling of the associated auscultatory sound sensors from skin of the thorax of the test-subject, wherein a debond-detection threshold is determined for each block of breath-held auscultatory sound time-series data, and the decoupling-detection process occurs after each block of breath-held auscultatory sound time-series data is acquired.
Figure 20:
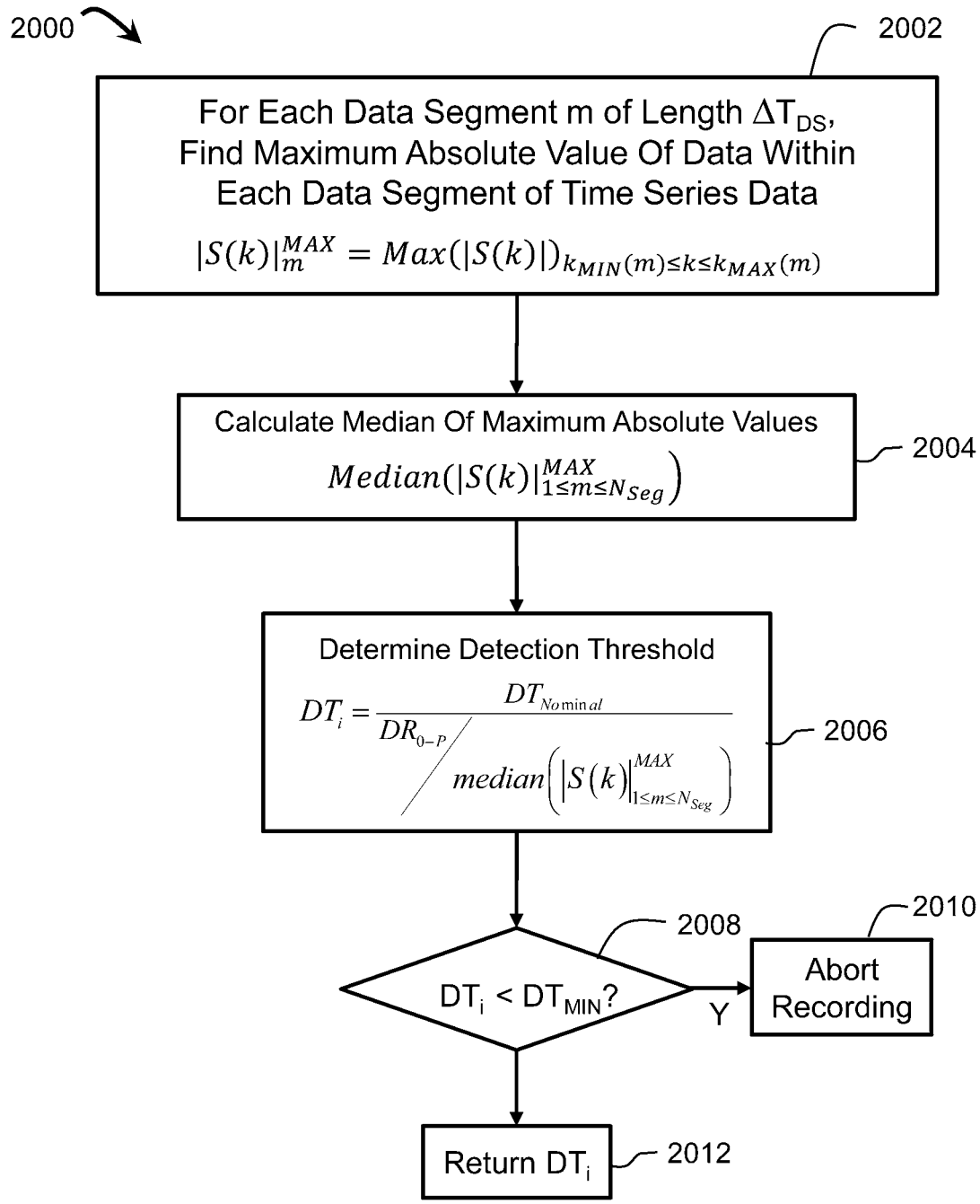
FIG. 20 illustrates a flowchart of a process for determining a debond-detection threshold, and that also provides for directly determining if the associated auscultatory sound sensor is detached from the skin of the test-subject, in accordance with the fourth aspect of the associated auscultatory-sound-sensing process.
Figure 21:
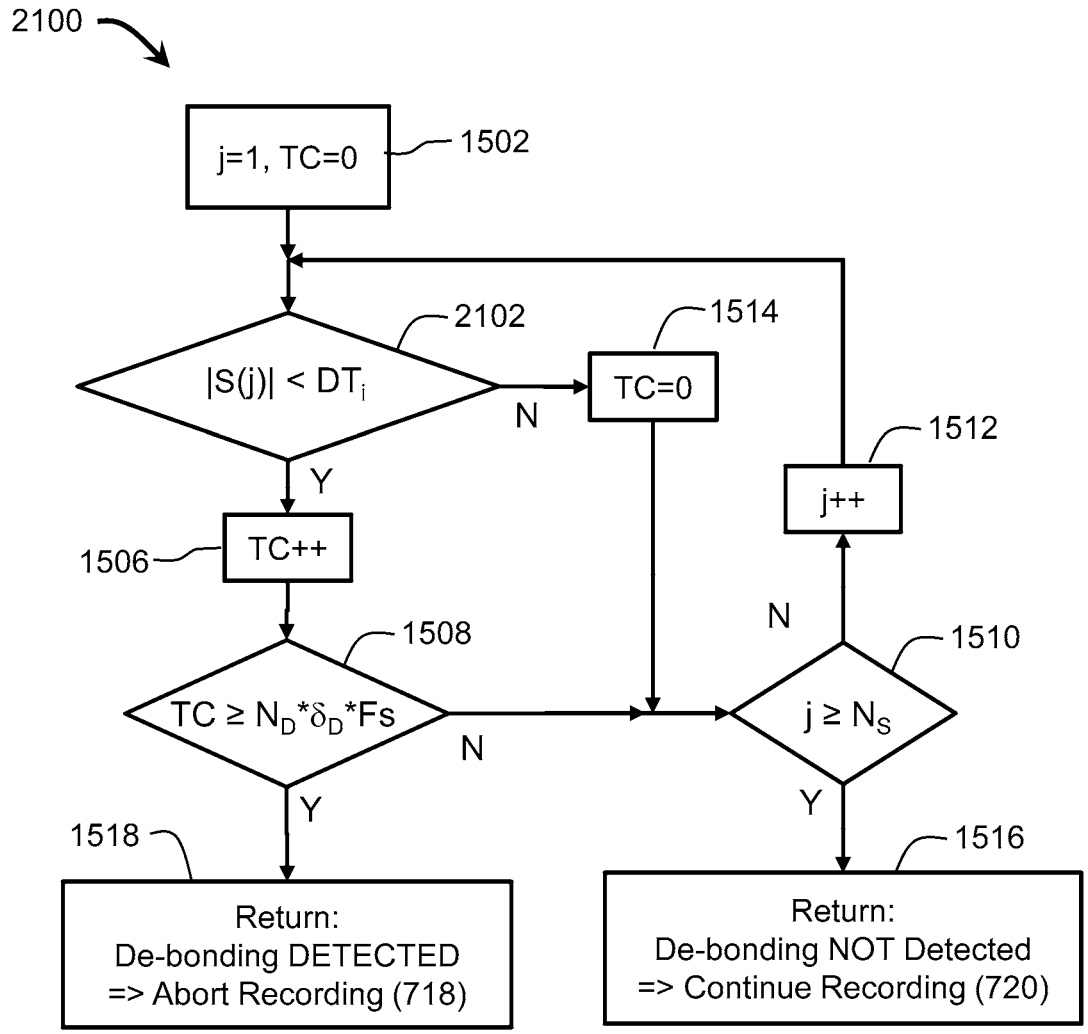
FIG. 21 illustrates a flowchart of a third aspect of a process for detecting whether or not an auscultatory sound sensor is debonded from the skin of a test-subject, in accordance with the fourth aspect of the associated auscultatory-sound-sensing process.

Referring to FIGS. 19-21, a fourth aspect 1900 of an auscultatory-sound-sensing process 1900 is substantially the same as the first aspect 700, except that the debond detection process is based upon unscaled auscultatory-sound-sensor time-series data S, and the process of determining whether or not the one or more auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ has become decoupled from the skin 38 of the thorax 20 of the test-subject 22 is responsive to a debond-detection threshold $DT_i$ that is determined separately for each associated block of auscultatory-sound-sensor time-series data S.

More particularly, referring to FIG. 19, the fourth aspect 1900 of the auscultatory-sound-sensing process 1900 is the same as the first aspect 700 illustrated in FIG. 7, except that step (706) is replaced with step (1902); in respect of debond detection, steps (712) and (714) are replaced with step (1904)—calling a debond-detection-threshold-determination process 2000—and step (1906)—calling a third aspect 2100 of a debond detection process 2100;—and the associated nose detection process of step (724) proceeds directly from step (710), in parallel with steps (1904) and (1906) that provide for debond detection.

More particularly, following the acquisition—in step (710)—of each block of auscultatory-sound-sensor time-series data S, in step (1904), the debond-detection-threshold-determination process 2000 is called to determine an associated debond-detection threshold $DT_i$. Referring to FIG. 20, the debond-detection-threshold-determination process 2000 commences with step (2002), wherein—as for the above-described scale-factor-determination process 1100—the block of auscultatory-sound-sensor time-series data S is divided into a plurality of data segments 46, for example, each of the same data-segment duration $\delta_D$ that nominally spans a single heartbeat, for example, about one second. For example, as indicated by X's in FIGS. 12a-12f, for each data segment 46, m spanning the range $k=k_{MIN}(m)$ to $k=k_{MAX}(m)$ of the auscultatory-sound-sensor time-series data $S(k)$, the corresponding maximum absolute value of the auscultatory-sound-sensor time-series data $S(k)$ is determined, as given by:

$$|S(k)|_m^{MAX} = \text{Max}(|S(k)|)_{k_{MIN}(m) \geq k \geq k_{MIN}(m)} \quad (6)$$

Then, in step (2004), the median of these maximum values is determined, as given by $$\text{median}(|S(k)|_{1 \leq m \geq N_{Seg}}^{MAX}) \quad (7)$$

Finally, in step (2006), the debond-detection threshold $DT_i$ is determined, as given by:

$$DT_i = \frac{DT_{Nominal}}{\frac{DR_{0-P}}{\text{median}(|S(k)|_{1 \leq m \leq N_{Seg}}^{MAX})}} \quad (8)$$

wherein $DR_{0-P}$ is the nominal zero-to-peak dynamic range of the auscultatory-sound-sensor time-series data S, and $DT_{Nominal}$ is the nominal value of the debond-detection threshold DT, for example, with the same value as the above-described predetermined debond-detection threshold DT. For example, in one set of embodiments, the nominal zero-to-peak dynamic range $DR_{0-P}$ is set to be 80% of the zero-to-peak range of the associated analog-to-digital converter used to digitize the auscultatory-sound-sensor time-series data S in step (818) (or step (806)).

If one or more of the associated auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ is detached from the skin 38 of the thorax 20 of the test-subject 22, then the associated level of the auscultatory sound signals 16 will be low—for example, at a noise level—resulting in a relatively low associated debond-detection threshold $DT_i$ from step (2006). Accordingly, if, in step (2008), the calculated debond-detection threshold $DT_i$ is less than an associated threshold $DT_{MIN}$, then the Data Recording Application (DRA) 14 is aborted in step (2010), and the operator 48 is alerted that the one or more auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ is/are detached, so that this can be remedied. Otherwise, from step (2008), if the value of the debond-detection threshold $DT_i$ meets or exceeds the associated threshold $DT_{MIN}$, in step (2012), the debond-detection threshold $DT_i$ is returned to step (1904) of the auscultatory-sound-sensing process 1900 for subsequent use in debond detection.

Referring again to FIG. 19, following step (1904) of the auscultatory-sound-sensing process 1900, and referring also to FIG. 21, in step (1906), a third aspect 2100 of the debond detection process 2100 is called, which is the same as the above-described first aspect 1500 of the debond detection process 1500 illustrated in FIG. 15, except that step (1504) thereof is replaced with step (2102). More particularly, in step (2102), if the absolute value of the sample of auscultatory-sound-sensor time-series data S is less than the debond-detection threshold $DT_i$, i.e. $|S(j)| < DT_i$, then in step (1506), the threshold counter TC is incremented. Otherwise, from step (2102), if the absolute value of the current sample of auscultatory-sound-sensor time-series data S is greater than or equal to the predetermined debond-detection threshold DT, i.e. $|S(j)| \geq DT_i$,—indicating that the auscultatory sound sensor 12, 12$^{1\prime\prime}$, 12$^{2\prime}$, 12$^{3\prime}$, 12$^{1\prime\prime}$, 12$^{2\prime\prime}$, 12$^{3\prime\prime}$ is not debonded from the skin 38 of the thorax 20 of the test-subject 22, then, in step (1514), the threshold counter TC is reset to a value of zero. Otherwise, for the remaining steps, the third aspect 2100 of the debond detection process 2100 is the same as the above-described first aspect 1500 of the debond detection process 1500, with the same consequences upon returning to the fourth aspect 1900 of an auscultatory-sound-sensing process 1900 depending upon whether or not one or more auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ are debonded from the skin 38 of the thorax 20 of the test-subject 22.

Figure 11:
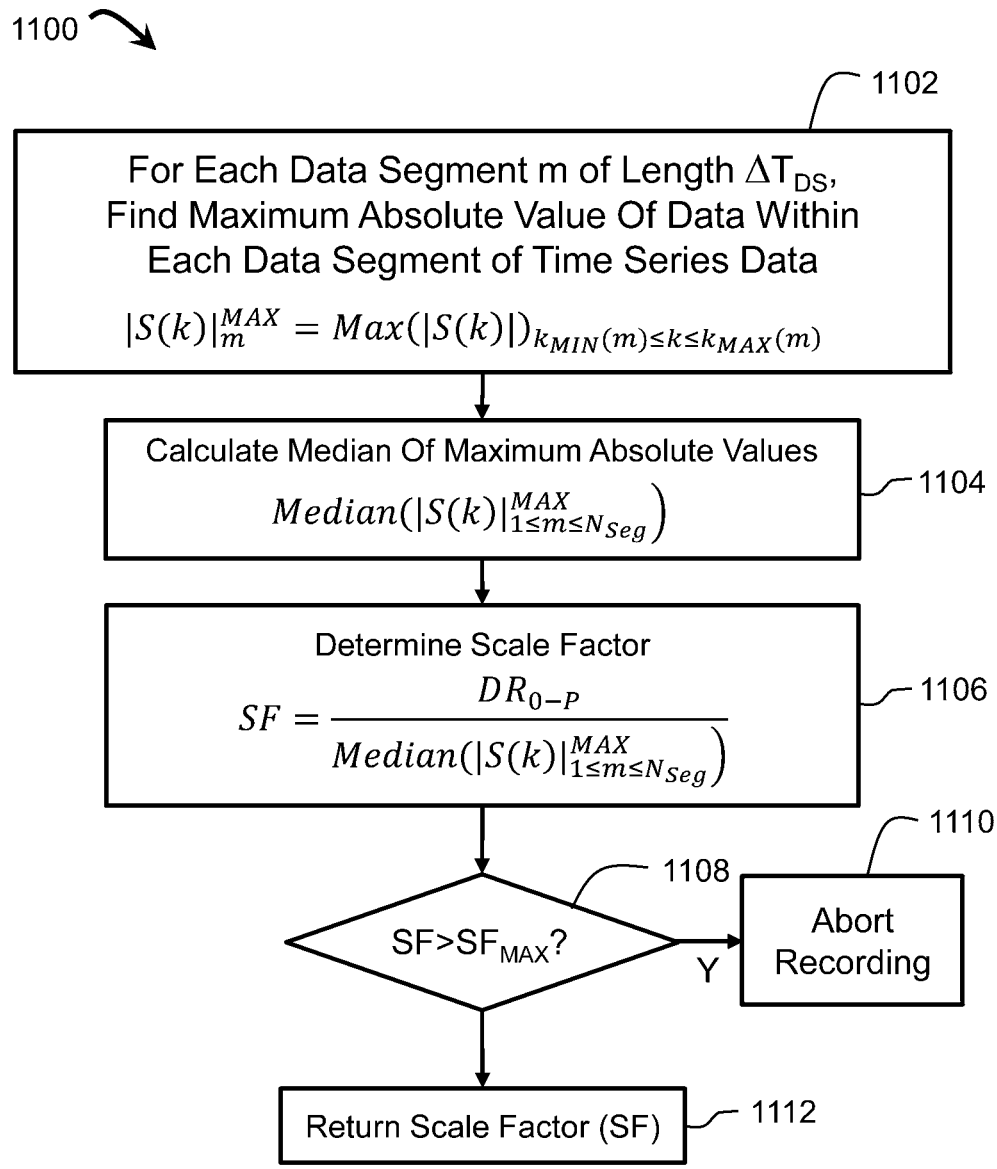
FIG. 11 illustrates a flowchart of a process for determining a scale factor used to scale auscultatory-sound-sensor time-series data, the latter of which is analyzed to detect whether or not the associated auscultatory sound sensor is decoupled from the skin of the test-subject, wherein the scale factor provides for directly determining if the associated auscultatory sound sensor is detached from the skin of the test-subject.

Returning to FIG. 19, in step (1902) of the auscultatory-sound-sensing process 1900, detachment of the one or more auscultatory sound sensors 12, 12$^{1\prime}$, 12$^{2\prime}$, 12$^{3\prime}$, 12$^{1\prime\prime}$, 12$^{2\prime\prime}$, 12$^{3\prime\prime}$ may be initially detected either by the scale-factor-determination process 1100 of FIG. 11, or by the debond detection process 2100 of FIG. 21, responsive to a block of auscultatory-sound-sensor time-series data S that is initially-acquired from step (704), without necessitating the test-subject 22 to hold their breath. However, given that the debond-detection threshold $DT_i$ is determined for each new block of auscultatory-sound-sensor time-series data S, steps (704) and (1902), are optional, although would still have utility in providing for an initial determination of whether or not one or more auscultatory sound sensors 12, $12^{1'}$, $12^{2'}$, $12^{3'}$, $12^{1''}$, $12^{2''}$, $12^{3''}$ is/are detached from the skin 38 of the thorax 20 of the test-subject 22, without requiring the test-subject 22 to hold their breath. Furthermore, alternatively, rather that determining the debond-detection threshold DT in step (1904) for each block of auscultatory-sound-sensor time-series data S, the debond-detection threshold DT could be determined initially in step (1902) for the first block of auscultatory-sound-sensor time-series data S, with that value then being used in step (1906) for subsequently acquired blocks of breath-held auscultatory-sound-sensor time-series data S—acquired in step (710)—to determine whether or not the associated auscultatory sound sensor 12, $12^{1'}$, $12^{2'}$, $12^{3'}$, $12^{1''}$, $12^{2''}$, $12^{3''}$ has debonded from the skin 38 of the thorax 20 of the test-subject 22.

Figure 22:
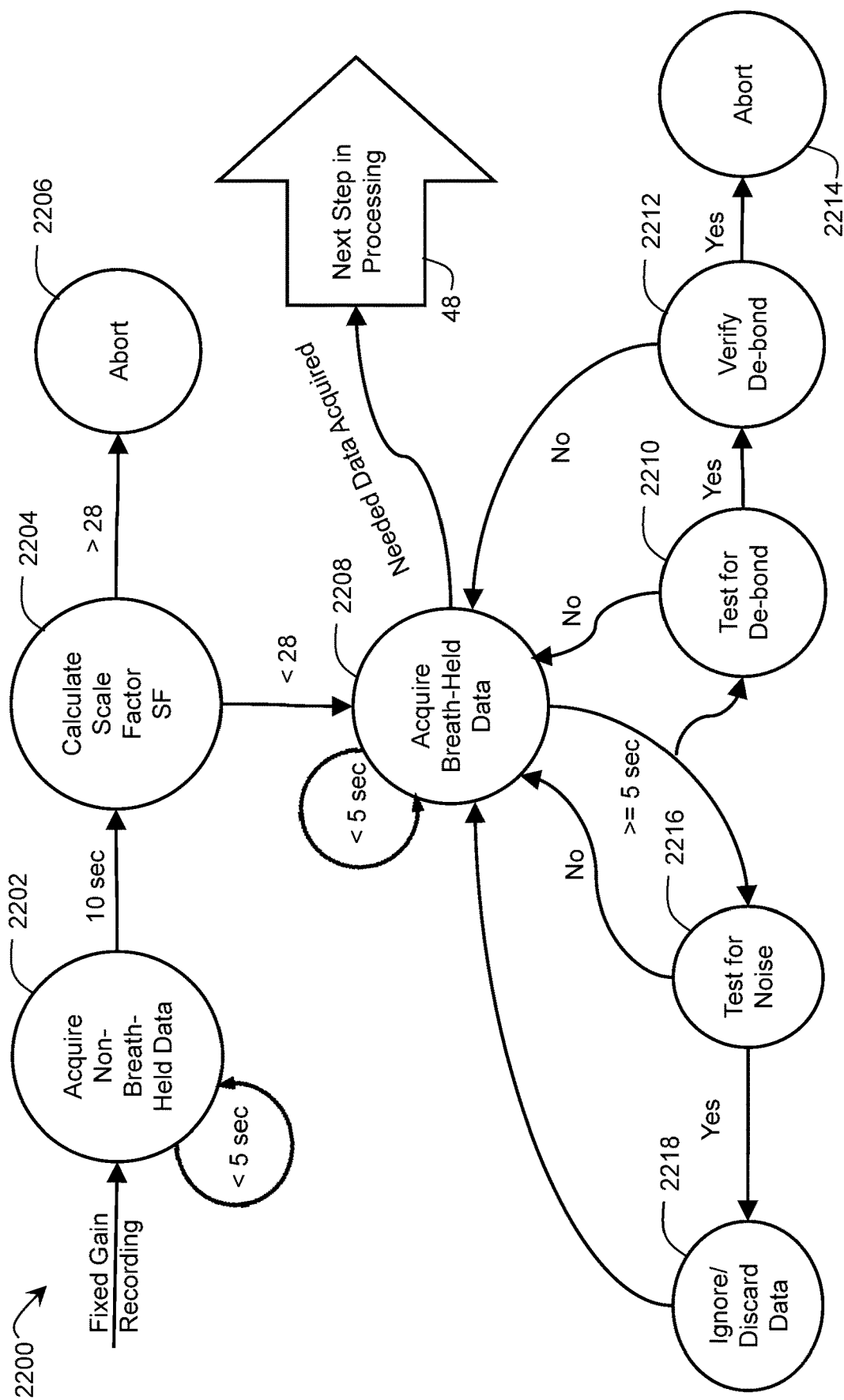
FIG. 22 illustrates a state-machine diagram representation of a fifth aspect of the auscultatory-sound-sensing process that incorporates a process for detecting a decoupling of the associated auscultatory sound sensors from the skin of the thorax of the test-subject, wherein the decoupling-detection process occurs after each block of breath-held auscultatory sound time-series data is acquired.

Referring to FIG. 22, a fifth aspect 2200 of an auscultatory-sound-sensing process 2200 is implemented as a state machine operating in accordance with a predetermined logic for transitioning from one state to another. For example, beginning with state (2202), the auscultatory sound signals 16 from one or more auscultatory sound sensors 12, $12^{1'}$, $12^{2'}$, $12^{3'}$, $12^{1''}$, $12^{2''}$, $12^{3''}$ are recorded at fixed gain for at least five seconds. After a predetermined interval, for example, ten seconds, the system transitions to state (2204), which calculates the scale factor SF, for example, in accordance with the above-described scale-factor-determination process 1100 illustrated in FIG. 11. If the resulting scale factor SF exceeds the predetermined threshold $SF_{MAX}$—indicative of one or more of the associated auscultatory sound sensors 12, $12^{1'}$, $12^{2'}$, $12^{3'}$, $12^{1''}$, $12^{2''}$, $12^{3''}$ being detached from the skin 38 of the thorax 20 of the test-subject 22,—then the system transitions to state (2206), wherein the Data Recording Application (DRA) 14 is aborted, and the operator 48 is alerted that the one or more auscultatory sound sensors 12, $12^{1'}$, $12^{2'}$, $12^{3'}$, $12^{1''}$, $12^{2''}$, $12^{3''}$ is/are detached, so that this can be remedied. Otherwise, from state (2204), if the resulting scale factor SF does not exceed the predetermined threshold $SF_{MAX}$—indicating that all of the associated auscultatory sound sensors 12, $12^{1'}$, $12^{2'}$, $12^{3'}$, $12^{1''}$, $12^{2''}$, $12^{3''}$ are attached to the skin 38 of the thorax 20 of the test-subject 22,—the system then transitions to state (2208), wherein a block of at least five seconds of breath-held auscultatory-sensor time-series data S is acquired from each of the one or more auscultatory sound sensors 12, $12^{1'}$, $12^{2'}$, $12^{3'}$, $12^{1''}$, $12^{2''}$, $12^{3''}$. After at least five seconds of recording, and either at the end of a predetermined recording interval or after the test-subject 22 resumes breathing, the system then transitions to state (2210), wherein the block(s) of auscultatory-sound-sensor time-series data S is/are tested to determine if any of the one or more auscultatory sound sensors 12, $12^{1'}$, $12^{2'}$, $12^{3'}$, $12^{1''}$, $12^{2''}$, $12^{3''}$ have debonded—based upon $N_{DT}$ successive data segments 46, and a corresponding total of $N_{DT}*\delta_D*Fs$ successive samples of breath-held auscultatory-sound-sensor time-series data S satisfying the associated debonding criteria, for example, of step (1504). If any of the one or more auscultatory sound sensors 12, $12^{1'}$, $12^{2'}$, $12^{3'}$, $12^{1''}$, $12^{2''}$, $12^{3''}$ appear to be debonded from the skin 38 of the thorax 20 of the test-subject 22, then the system transitions to state (2212), wherein immediately-subsequent portions of the block(s) of auscultatory-sound-sensor time-series data S are tested to validate this—based upon $N_{DV}$ successive data segments 46, and a corresponding total of $N_{DV}*\delta_D*Fs$ successive samples of breath-held auscultatory-sound-sensor time-series data S. If any of the one or more auscultatory sound sensors 12, $12^{1'}$, $12^{2'}$, $12^{3'}$, $12^{1''}$, $12^{2''}$, $12^{3''}$ are confirmed to have debonded, then the system then transitions to state (2214), wherein the Data Recording Application (DRA) 14 is aborted, and the operator 48 is alerted that one or more auscultatory sound sensors 12, $12^{1'}$, $12^{2'}$, $12^{3'}$, $12^{1''}$, $12^{2''}$, $12^{3''}$ is/are detached, so that this can be remedied.

Otherwise, either from either states (2210) or (2212), if none of the one or more auscultatory sound sensors 12, $12^{1'}$, $12^{2'}$, $12^{3'}$, $12^{1''}$, $12^{2''}$, $12^{3''}$ are debonded from the skin 38 of the thorax 20 of the test-subject 22, then the system transitions back to state (2208) to acquire an additional subsequent set of one or more block(s) of auscultatory-sound-sensor time-series data S following completion of states (2216) or (2218), the latter of which are described hereinbelow. For example, in the above-described first through fourth aspects 700, 1600, 1800, 1900 of the auscultatory-sound-sensing process 700, 1600, 1800, 1900, the test and validation phases of states (2210) and (2212), respectively, are effectively merged into a single debond detection process 1500, 1700/(1706) et seq., 2100, wherein the above-described value of $N_D$ used in the first through fourth aspects 700, 1600, 1800, 1900 is equal to the sum of $N_{DT}$ and $N_{DV}$, i.e. $N_D = N_{DT} \pm N_{DV}$. In parallel with the transition to state (2210) from state (2208), or separately prior to acquisition of a subsequent set of one or more block(s) of auscultatory-sound-sensor time-series data S in step (2208), the system also transitions from state (2208) to state (2216) to test the block(s) of auscultatory-sound-sensor time-series data S for noise, and if excessive noise is detected, to then transition to state (2218), that latter of which causes the currently-acquired block(s) of auscultatory-sound-sensor time-series data S to be either discarded or ignored, followed by a subsequent transition back to state (2208) to acquire another set of one or more block(s) of auscultatory-sound-sensor time-series data S from the associated one or more auscultatory sound sensors 12, $12^{1'}$, $12^{2'}$, $12^{3'}$, $12^{1''}$, $12^{2''}$, $12^{3''}$. Otherwise, if excessive noise is not detected in step (2216), then the system transitions back to step (2208) to acquire a subsequent block of auscultatory-sound-sensor time-series data S if no debonding is, or has been, detected for the current block of auscultatory-sound-sensor time-series data S. If, from state (2208)—after testing for debonding and noise—a sufficient total duration of blocks of auscultatory-sound-sensor time-series data S are neither corrupted by noise, nor compromised by a debonding of one or more auscultatory sound sensors 12, $12^{1'}$, $12^{2'}$, $12^{3'}$, $12^{1''}$, $12^{2''}$, $12^{3''}$, then the system outputs the acquired composite of blocks of auscultatory-sound-sensor time-series data S to the Data Analysis Application (DAA) 54 for subsequent processing and analysis.

Referring again to FIG. 1, in accordance with one set of embodiments, the results from the docking system 27 may be transferred to a server computer system 56, for example, for subsequent transfer to an external data storage or processing system 58, for example, to provide for either viewing or analyzing the results at a remote location. Referring again to FIGS. 2 and 4, in one set of embodiments, the composite set of blocks of breath-held auscultatory-sound-sensor time-series data S are screened prior to analysis by the associated Data Analysis Application (DAA) 54, for example, by first segmenting the set of blocks of breath-held auscultatory-sound-sensor time-series data S by heart cycle with an associated segmentation process 60, and then validating the associated heart cycle data with an associated heart cycle validation process 62, for example, to provide for additional screening for heart-phase associated noise.

While specific embodiments have been described in detail in the foregoing detailed description and illustrated in the accompanying drawings, those with ordinary skill in the art will appreciate that various modifications and alternatives to those details could be developed in light of the overall teachings of the disclosure. It should be understood, that any reference herein to the term "or" is intended to mean an "inclusive or" or what is also known as a "logical OR", wherein when used as a logic statement, the expression "A or B" is true if either A or B is true, or if both A and B are true, and when used as a list of elements, the expression "A, B or C" is intended to include all combinations of the elements recited in the expression, for example, any of the elements selected from the group consisting of A, B, C, (A, B), (A, C), (B, C), and (A, B, C); and so on if additional elements are listed. Furthermore, it should also be understood that the indefinite articles "a" or "an", and the corresponding associated definite articles "the' or "said", are each intended to mean one or more unless otherwise stated, implied, or physically impossible. Yet further, it should be understood that the expressions "at least one of A and B, etc.", "at least one of A or B, etc.", "selected from A and B, etc." and "selected from A or B, etc." are each intended to mean either any recited element individually or any combination of two or more elements, for example, any of the elements from the group consisting of "A", "B", and "A AND B together", etc. Yet further, it should be understood that the expressions "one of A and B, etc." and "one of A or B, etc." are each intended to mean any of the recited elements individually alone, for example, either A alone or B alone, etc., but not A AND B together. Furthermore, it should also be understood that unless indicated otherwise or unless physically impossible, that the above-described embodiments and aspects can be used in combination with one another and are not mutually exclusive. Accordingly, the particular arrangements disclosed are meant to be illustrative only and not limiting as to the scope of the invention, which is to be given the full breadth of any claims that are supportable by the specification and drawings, and any and all equivalents thereof.

The invention claimed is:

1. A method, comprising:
    a. acquiring at least one block of time-series data, wherein each said at least one block of time-series data comprises a plurality of samples of an auscultatory-sound signal generated by an auscultatory-sound sensor operatively coupled to a portion of the skin of a test-subject;
    b. determining at least one comparison value selected from the group consisting of at least one data-dependent scale factor and at least one data-dependent detection threshold, wherein the operation of determining said at least one comparison value is responsive to said at least one block of time-series data, and said at least one comparison value provides a measure of a range of values of said at least one block of time-series data in relation to a predetermined metric; and
    c. determining whether or not said auscultatory-sound sensor is either debonded or detached from said skin of said test-subject responsive to at least one of said at least one comparison value.

2. A method as recited in claim 1, wherein the operation of determining at least one of said at least one comparison value comprises determining said at least one data-dependent scale factor responsive to a corresponding said at least one block of time-series data, wherein the value of said at least one data-dependent scale factor is determined so that the values of said plurality of samples of said corresponding at least one block of time-series data, when multiplied by said at least one data-dependent scale factor, are nominally within a dynamic range of an associated data acquisition system used to acquire said at least one block of time-series data.

3. A method as recited in claim 2, wherein the operation of determining said at least one data-dependent scale factor comprises:
    a. segmenting said at least one block of time-series data into a plurality of time-series segments;
    b. determining a plurality of peak absolute values of said auscultatory-sound signal, wherein each peak absolute value of said plurality of peak absolute values of said auscultatory-sound signal corresponds to a peak absolute value of said auscultatory-sound signal within a corresponding time-series segment of said plurality of time-series segments; and
    c. determining a median value of said plurality of peak absolute values of said auscultatory-sound signal, wherein said at least one data-dependent scale factor is inversely related to said median value of said plurality of peak absolute values of said auscultatory-sound signal.

4. A method as recited in claim 3, wherein a time period spanned by each time-series segment of said plurality of time-series segments of said at least one block of time-series data is nominally about one heart cycle.

5. A method as recited in claim 3, wherein said at least one data-dependent scale factor is responsive to a ratio of said dynamic range of said associated data acquisition system used to acquire said auscultatory-sound signal, divided by said median value of said plurality of peak absolute values of said auscultatory-sound signal.

6. A method as recited in claim 5, wherein said dynamic range is a fraction of a zero-to-peak range of said associated data acquisition system.

7. A method as recited in claim 6, wherein said fraction is in the range of 0.65 to 0.95.

8. A method as recited in claim 2, further comprising comparing said at least one data-dependent scale factor with a detachment threshold, and determining whether or not said auscultatory-sound sensor is detached from said skin of said test-subject responsive to whether or not said at least one data-dependent scale factor exceeds said detachment threshold.

9. A method as recited in claim 8, wherein if said auscultatory-sound sensor is determined to be detached from said skin of said test-subject, then either aborting the acquisition, or nullifying a recording, of said at least one block of time-series data.

10. A method as recited in claim 2, wherein the operation of determining at least one said at least one data-dependent scale factor responsive to said corresponding said at least one block of time-series data comprises determining a nominal data-dependent scale factor responsive to one block of time-series data of said at least one block of time-series data, and the operation of determining whether or not said auscultatory-sound sensor is either debonded or detached from said skin of said test-subject is both responsive to said nominal data-dependent scale factor determined from said one block of time-series data, and responsive to one or more blocks of said time-series data recorded while said test-subject was holding their breath.

11. A method as recited in claim 10, wherein the operation of determining whether or not said auscultatory-sound sensor is debonded from said skin of said test-subject comprises, for each successive value of successive samples of said auscultatory sound signal, from said one or more blocks of said time-series data:

a. for each of said successive samples of said auscultatory sound signal, comparing a scaled value of said successive value with a predetermined detection threshold, wherein said scaled value is determined by multiplying said successive value by said nominal data-dependent scale factor; and d. providing an indication that said auscultatory-sound sensor is debonded from said skin of said test-subject if the number of said successive samples of said auscultatory sound signal for which said scaled value is less than said predetermined detection threshold is greater than a count threshold.

12. A method as recited in claim 11, wherein the operation of comparing said scaled value with said predetermined detection threshold comprises comparing an absolute value of said scaled value with said predetermined detection threshold.

13. A method as recited in claim 11, wherein the operation of comparing said scaled value with said predetermined detection threshold is performed for each sample during the operation of acquiring said at least one block of time-series data.

14. A method as recited in claim 11, wherein if said auscultatory-sound sensor is determined to be debonded from said skin of said test-subject, then either aborting the acquisition, or nullifying a recording, of said at least one block of time-series data.

15. A method as recited in claim 2, wherein the operation of determining at least one said at least one data-dependent scale factor responsive to said corresponding said at least one block of time-series data comprises determining a plurality of data-dependent scale factors, wherein each data-dependent scale factor of said plurality of data-dependent scale factors is responsive to a corresponding associated said at least one block of time-series data in one-to-one relationship therewith, and the operation of determining whether or not said auscultatory-sound sensor is either debonded or detached from said skin of said test-subject is both responsive to at least one said data-dependent scale factor, and responsive to said corresponding associated said at least one said block of time-series data recorded while said test-subject was holding their breath.

16. A method as recited in claim 1, wherein the operation of determining at least one of said at least one comparison value comprises determining said at least one data-dependent detection threshold responsive to a corresponding said at least one block of time-series data, wherein the value of said at least one data-dependent detection threshold is responsive to a nominal detection threshold scaled by a measure responsive to a range of values of corresponding samples said at least one block of time-series data, wherein said nominal detection threshold is responsive to a dynamic range of an associated data acquisition system used to acquire said at least one block of time-series data.

17. A method as recited in claim 16, wherein the operation of determining said at least one data-dependent detection threshold comprises:

a. segmenting said at least one block of time-series data into a plurality of time-series segments;

b. determining a plurality of peak absolute values of said auscultatory-sound signal, wherein each peak absolute value of said plurality of peak absolute values of said auscultatory-sound signal corresponds to a peak absolute value of said auscultatory-sound signal within a corresponding time-series segment of said plurality of time-series segments;

c. determining a median value of said plurality of peak absolute values of said auscultatory-sound signal, wherein said at least one data-dependent detection threshold is directly related to said median value of said plurality of peak absolute values of said auscultatory-sound signal.

18. A method as recited in claim 17, wherein a time period spanned by each time-series segment of said plurality of time-series segments of said at least one block of time-series data is nominally about one heart cycle.

19. A method as recited in claim 17, wherein said at least one data-dependent detection threshold is inversely responsive to a ratio of said dynamic range of said associated data acquisition system used to acquire said auscultatory-sound signal, divided by said median value of said plurality of peak absolute values of said auscultatory-sound signal.

20. A method as recited in claim 19, wherein said dynamic range is a fraction of a zero-to-peak range of said associated data acquisition system.

21. A method as recited in claim 20, wherein said fraction is in the range of 0.65 to 0.95.

22. A method as recited in claim 16, further comprising comparing said at least one data-dependent detection threshold with a detachment threshold, and determining whether or not said auscultatory-sound sensor is detached from said skin of said test-subject responsive to whether or not said at least one data-dependent detection threshold is less then said detachment threshold.

23. A method as recited in claim 22, wherein if said auscultatory-sound sensor is determined to be detached from said skin of said test-subject, then either aborting the acquisition, or nullifying a recording, of said at least one block of time-series data.

24. A method as recited in claim 16, wherein the operation of determining whether or not said auscultatory-sound sensor is either debonded or detached from said skin of said test-subject is both responsive to at least one said at least one data-dependent detection threshold, and responsive to one or more blocks of said time-series data recorded while said test-subject was holding their breath.

25. A method as recited in claim 16, wherein the operation of determining whether or not said auscultatory-sound sensor is debonded from said skin of said test-subject comprises, for each successive value of successive samples of said auscultatory sound signal, from one or more blocks of said time-series data:

d. for each of said successive samples of said auscultatory sound signal, comparing said successive value with said at least one data-dependent detection threshold, and e. providing an indication that said auscultatory-sound sensor is debonded from said skin of said test-subject if the number of said successive samples of said auscultatory sound signal for which said successive value is less than said at least one data-dependent detection threshold is greater than a count threshold.

26. A method as recited in claim 25, wherein the operation of comparing said successive value with said at least one data-dependent detection threshold comprises comparing an absolute value of said successive value with said at least one data-dependent detection threshold.

27. A method as recited in claim 25, wherein if said auscultatory-sound sensor is determined to be debonded from said skin of said test-subject, then either aborting the acquisition, or nullifying a recording, of said at least one block of time-series data.

\* \* \* \* \*